United States Patent
Ndhlovu et al.

(10) Patent No.: US 11,912,772 B2
(45) Date of Patent: Feb. 27, 2024

(54) ANTI-GALECTIN-9 ANTIBODY AND METHODS OF USE THEREOF

(71) Applicant: University of Hawaii, Honolulu, HI (US)

(72) Inventors: Lishomwa C. Ndhlovu, Honolulu, HI (US); Toshiro Niki, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 664 days.

(21) Appl. No.: 17/260,077

(22) PCT Filed: Jul. 12, 2019

(86) PCT No.: PCT/US2019/041557
§ 371 (c)(1),
(2) Date: Jan. 13, 2021

(87) PCT Pub. No.: WO2020/018364
PCT Pub. Date: Jan. 23, 2020

(65) Prior Publication Data
US 2021/0324086 A1     Oct. 21, 2021

Related U.S. Application Data

(60) Provisional application No. 62/698,584, filed on Jul. 16, 2018.

(51) Int. Cl.
| | |
|---|---|
| *C07K 16/28* | (2006.01) |
| *A61K 39/00* | (2006.01) |
| *A61K 45/06* | (2006.01) |
| *A61P 35/00* | (2006.01) |
| *C07K 14/47* | (2006.01) |

(52) U.S. Cl.
CPC .......... *C07K 16/2851* (2013.01); *A61K 45/06* (2013.01); *A61P 35/00* (2018.01); *A61K 2039/505* (2013.01)

(58) Field of Classification Search
None
See application file for complete search history.

(56) References Cited

U.S. PATENT DOCUMENTS

| | | | |
|---|---|---|---|
| 2012/0282251 A1 | 11/2012 | Tremblay et al. | |
| 2017/0275374 A1 | 9/2017 | Schiffer-Mannioul | |
| 2017/0283499 A1* | 10/2017 | Delhem | A61P 35/00 |

FOREIGN PATENT DOCUMENTS

WO    WO-2016139297 A1 *  9/2016  ......... A61K 38/1709

OTHER PUBLICATIONS

Bertino, P., Premeaux, T.A., Fujita, T., Haun, B.K., Marciel, M.P., Hoffmann, F.W., Garcia, A., Yiang, H., Pastorino, S., Carbone, M., Niki, et al . . . Targeting the C-terminus of galectin-9 induces mesothelioma apoptosis and M2 macrophage depletion. 2019. Oncoimmunology. 8(1482) 1-12. (Year: 2019).*
Barjon, C. et al. (2012) "A novel monoclonal antibody for detection of galectin-9 in tissue sections: application to human tissues infected by oncogenic viruses." Infectious Agents and Cancer 7(16):1-11.
International Preliminary Report on Patentability in PCT/US2019/041557 dated Jan. 19, 2021.
International Search Report and Written Opinion in PCT/US2019/041557 dated Oct. 4, 2019.

* cited by examiner

*Primary Examiner* — Daniel E Kolker
*Assistant Examiner* — Maureen Varina Driscoll
(74) *Attorney, Agent, or Firm* — LICATA & TYRRELL P.C.

(57) ABSTRACT

An antibody targeting Galectin-9 is provided as are methods of using the same treatment of chronic immune conditions such as infections, inflammatory diseases and cancer, in particular malignant mesothelioma.

16 Claims, 2 Drawing Sheets

Specification includes a Sequence Listing.

SEQUENCE LISTING

<160> NUMBER OF SEQ ID NOS: 11

<210> SEQ ID NO 1
<211> LENGTH: 8
<212> TYPE: PRT
<213> ORGANISM: Artificial sequence
<220> FEATURE:

```
<223> OTHER INFORMATION: Synthetic peptide

<400> SEQUENCE: 1

Gly Tyr Thr Phe Thr Asn Phe Gly
1               5

<210> SEQ ID NO 2
<211> LENGTH: 8
<212> TYPE: PRT
<213> ORGANISM: Artificial sequence
<220> FEATURE:
<223> OTHER INFORMATION: Synthetic peptide

<400> SEQUENCE: 2

Ile Asn Thr Tyr Lys Gly Val Pro
1               5

<210> SEQ ID NO 3
<211> LENGTH: 14
<212> TYPE: PRT
<213> ORGANISM: Artificial sequence
<220> FEATURE:
<223> OTHER INFORMATION: Synthetic peptide

<400> SEQUENCE: 3

Ala Arg Arg Lys Asp Gly Asp Asp Tyr Tyr Ala Met Asp Tyr
1               5                   10

<210> SEQ ID NO 4
<211> LENGTH: 8
<212> TYPE: PRT
<213> ORGANISM: Artificial sequence
<220> FEATURE:
<223> OTHER INFORMATION: Synthetic peptide

<400> SEQUENCE: 4

Gln Ser Leu Phe Asn Ser Arg Thr
1               5

<210> SEQ ID NO 5
<211> LENGTH: 3
<212> TYPE: PRT
<213> ORGANISM: Artificial sequence
<220> FEATURE:
<223> OTHER INFORMATION: Synthetic peptide

<400> SEQUENCE: 5

Trp Ala Ser
1

<210> SEQ ID NO 6
<211> LENGTH: 8
<212> TYPE: PRT
<213> ORGANISM: Artificial sequence
<220> FEATURE:
<223> OTHER INFORMATION: Synthetic peptide

<400> SEQUENCE: 6

Lys Gln Ser Tyr Asn Gln Trp Thr
1               5

<210> SEQ ID NO 7
<211> LENGTH: 114
<212> TYPE: PRT
<213> ORGANISM: Artificial sequence
<220> FEATURE:
<223> OTHER INFORMATION: Synthetic polypeptide
```

<400> SEQUENCE: 7

Gln Val Gln Leu Lys Glu Ser Gly Glu Thr Val Lys Ile Ser Cys Lys
1               5                   10                  15

Ala Ser Gly Tyr Thr Phe Thr Asn Phe Gly Met Asn Trp Val Arg Gln
            20                  25                  30

Ser Pro Arg Lys Asp Leu Lys Trp Leu Gly Trp Ile Asn Thr Tyr Lys
        35                  40                  45

Gly Val Pro Lys Tyr Ala Asp Asp Phe Lys Gly Arg Phe Ala Phe Ser
    50                  55                  60

Leu Glu Thr Ser Ala Ser Thr Ala Tyr Leu Gln Ile Asn Asn Leu Lys
65                  70                  75                  80

Asn Glu Asp Thr Ala Thr Tyr Phe Cys Ala Arg Arg Lys Asp Gly Asp
                85                  90                  95

Asp Tyr Tyr Ala Met Asp Tyr Trp Gly Gln Gly Thr Ser Val Thr Val
            100                 105                 110

Ser Ser

<210> SEQ ID NO 8
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 8

Ser Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Ala Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Thr Val Gln Ala Glu Asp Leu Ala Phe Tyr Phe Cys Lys Gln
                85                  90                  95

Ser Tyr Asn Gln Trp Thr Phe Gly Gly Gly Thr Lys Leu Glu Ile Lys
            100                 105                 110

<210> SEQ ID NO 9
<211> LENGTH: 323
<212> TYPE: PRT
<213> ORGANISM: Homo sapiens

<400> SEQUENCE: 9

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

```
Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln Pro Pro Gly Val Trp Pro Ala Asn Pro Ala Pro Ile
145                 150                 155                 160

Thr Gln Thr Val Ile His Thr Val Gln Ser Ala Pro Gly Gln Met Phe
                165                 170                 175

Ser Thr Pro Ala Ile Pro Pro Met Met Tyr Pro His Pro Ala Tyr Pro
            180                 185                 190

Met Pro Phe Ile Thr Thr Ile Leu Gly Gly Leu Tyr Pro Ser Lys Ser
        195                 200                 205

Ile Leu Leu Ser Gly Thr Val Leu Pro Ser Ala Gln Arg Phe His Ile
    210                 215                 220

Asn Leu Cys Ser Gly Asn His Ile Ala Phe His Leu Asn Pro Arg Phe
225                 230                 235                 240

Asp Glu Asn Ala Val Val Arg Asn Thr Gln Ile Asp Asn Ser Trp Gly
                245                 250                 255

Ser Glu Glu Arg Ser Leu Pro Arg Lys Met Pro Phe Val Arg Gly Gln
            260                 265                 270

Ser Phe Ser Val Trp Ile Leu Cys Glu Ala His Cys Leu Lys Val Ala
        275                 280                 285

Val Asp Gly Gln His Leu Phe Glu Tyr Tyr His Arg Leu Arg Asn Leu
    290                 295                 300

Pro Thr Ile Asn Arg Leu Glu Val Gly Gly Asp Ile Gln Leu Thr His
305                 310                 315                 320

Val Gln Thr

<210> SEQ ID NO 10
<211> LENGTH: 322
<212> TYPE: PRT
<213> ORGANISM: Mus musculus

<400> SEQUENCE: 10

Met Ala Leu Phe Ser Ala Gln Ser Pro Tyr Ile Asn Pro Ile Ile Pro
1               5                   10                  15

Phe Thr Gly Pro Ile Gln Gly Gly Leu Gln Glu Gly Leu Gln Val Thr
                20                  25                  30

Leu Gln Gly Thr Thr Lys Ser Phe Ala Gln Arg Phe Val Val Asn Phe
            35                  40                  45

Gln Asn Ser Phe Asn Gly Asn Asp Ile Ala Phe His Phe Asn Pro Arg
        50                  55                  60

Phe Glu Glu Gly Gly Tyr Val Val Cys Asn Thr Lys Gln Asn Gly Gln
65                  70                  75                  80

Trp Gly Pro Glu Glu Arg Lys Met Gln Met Pro Phe Gln Lys Gly Met
                85                  90                  95

Pro Phe Glu Leu Cys Phe Leu Val Gln Arg Ser Glu Phe Lys Val Met
            100                 105                 110

Val Asn Lys Lys Phe Phe Val Gln Tyr Gln His Arg Val Pro Tyr His
        115                 120                 125
```

```
Leu Val Asp Thr Ile Ala Val Ser Gly Cys Leu Lys Leu Ser Phe Ile
    130                 135                 140
Thr Phe Gln Thr Gln Asp Phe Arg Pro Ala His Gln Ala Pro Met Ala
145                 150                 155                 160
Gln Thr Thr Ile His Met Val His Ser Thr Pro Gly Gln Met Phe Ser
                165                 170                 175
Thr Pro Gly Ile Pro Pro Val Val Tyr Pro Thr Pro Ala Tyr Thr Ile
            180                 185                 190
Pro Phe Tyr Thr Pro Ile Pro Asn Gly Leu Tyr Pro Ser Lys Ser Ile
        195                 200                 205
Met Ile Ser Gly Asn Val Leu Pro Asp Ala Thr Arg Phe His Ile Asn
    210                 215                 220
Leu Arg Cys Gly Gly Asp Ile Ala Phe His Leu Asn Pro Arg Phe Asn
225                 230                 235                 240
Glu Asn Ala Val Val Arg Asn Thr Gln Ile Asn Asn Ser Trp Gly Gln
                245                 250                 255
Glu Glu Arg Ser Leu Leu Gly Arg Met Pro Phe Ser Arg Gly Gln Ser
            260                 265                 270
Phe Ser Val Trp Ile Ile Cys Glu Gly His Cys Phe Lys Val Ala Val
        275                 280                 285
Asn Gly Gln His Met Cys Glu Tyr Tyr His Arg Leu Lys Asn Leu Gln
    290                 295                 300
Asp Ile Asn Thr Leu Glu Val Ala Gly Asp Ile Gln Leu Thr His Val
305                 310                 315                 320
Gln Thr

<210> SEQ ID NO 11
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 11
cagcacatta gggagcttac acg                                          23
```

ANTI-GALECTIN-9 ANTIBODY AND METHODS OF USE THEREOF

INTRODUCTION

This application is a U.S. National Stage Application of International Application Serial Number PCT/US2019/041557 filed Jul. 12, 2019 and claims benefit of priority to U.S. Provisional Patent Application Ser. No. 62/698,584, filed Jul. 16, 2018, the contents of each of which are incorporated herein by reference in their entirety.

This invention was made with government support under grant no. MH112457, awarded by the National Institutes of Health. The government has certain rights in this invention.

BACKGROUND

Galectin-9 is classified as a tandem-repeat type Galectin, which is composed of two distinct β-galactoside binding sites linked by a peptide. The N-terminal carbohydrate recognition domain (CRD) is composed of 148 amino acids and the C-terminal CRD is composed of 146 amino acids. Both N- and C-terminal CRDs have carbohydrate-binding pockets that differ in amino acid sequence from each other, resulting in differential affinity to β-galactosides and distinct physiologic activities (Tureci, et al. (1997) *J. Biol. Chem.* 272:6416-6422; Wada & Kanwar (1997) *J. Biol. Chem.* 272:6078-6086; Bi, et al. (2008) *J. Biol. Chem.* 283:12248-12258; Li, et al. (2011) *Mol. Immunol.* 48:670-677).

Galectin-9 has recently emerged as a candidate for cancer treatment. Elevated Galectin-9 levels have been in observed a wide range of cancers, including melanoma, Hodgkin's lymphoma, hepatocellular, pancreatic, gastric, colon and clear cell renal cell cancers (Wdowiak, et al. (2018) *Int. J. Mol. Sci.* 19:210). In renal cancer, patients with high Galectin-9 expression show more advanced progression of the disease with larger tumor size and necrosis (Kawashima, et al. (2014) *BJU Int.* 113:320-332). In melanoma cancer, considered one of the most lethal cancers due to its aggressive metastasis and resistance to therapy, Galectin-9 is expressed in 57% of tumors and is significantly increased in the plasma of patients with advanced melanoma compared to healthy controls (Enninga, et al. (2016) *Melanoma Res.* 26(5):429-441). A number of studies have shown utility for Galectin-9 as a prognostic marker, and more recently as a drug target (Kageshita, et al. (2002) *Int. J. Cancer.* 99(6):809-16), e.g., inhibited via the use of anti-Galectin-9 antibodies (US 2019/0127472 A1). Further, both in vitro and in vivo studies show that a recombinant version of Galectin-9 induces apoptosis of tumor cells, such as hematologic malignant cells (Kuroda, et al. (2010) *Mol. Cancer Res.* 8:994-1001; Kobayashi, et al. (2010) *Leukemia* 24:843-850), melanoma (Wiersma, et al. (2012) *J. Invest. Dermatol.* 132:2302-2305) and gastrointestinal tumors (Fujita, et al. (2015) *Int. J. Oncol.* 46:2419-2430; Kobayashi, et al. (2015) *Oncol. Rep.* 34:1761-1770; Tadokoro, et al. (2016) *Int. J. Oncol.* 48:1165-1174; Takano, et al. (2016) *Oncol. Rep.* 35:851-860). Studies with immune cells suggest that recombinant Galectin-9 could also alter the tumor microenvironment, although it was unclear if this modulation leads to an anti-tumor or pro-tumor effect (Wada, et al. (1997) *J. Clin. Invest.* 99:2452-2461; Kashio, et al. (2003) *J. Immunol.* 170:3631-3636). When fully differentiated from naïve T cells, T helper type 1 (TH1) cells express a counter-receptor for Galectin-9, Tim-3. Galectin-9/Tim-3 interactions lead to TH1 cell apoptosis and reduced TH1 immunity (Zhu, et al. (2005) *Nat. Immunol.* 6:1245-1252). Galectin-9 also induces apoptosis of B cells, which do not express Tim-3 on the cell surface. In macrophages, the role of Galectin-9 is less clear with some studies reporting apoptosis and others activation involving the dectin-1 innate immune receptor (Daley, et al. (2017) *Nat. Med.* 23:556-567).

SUMMARY OF THE INVENTION

This invention provides an isolated antibody, or an antigen binding fragment of the antibody, which binds human Galectin-9, wherein the antibody has (a) a heavy chain variable region including (i) a CDR1 of SEQ ID NO:1; (ii) a CDR2 of SEQ ID NO:2; and (iii) a CDR3 of SEQ ID NO:3; and (b) a light chain variable region including (i) a CDR1 of SEQ ID NO:4, (ii) a CDR2 of SEQ ID NO:5, and (iii) a CDR3 of SEQ ID NO:6. In some embodiments, the antibody has a heavy chain variable region of SEQ ID NO:7 and a light chain variable region of SEQ ID NO:8. A pharmaceutical composition including the antibody or antigen binding fragment, as well as an isolated nucleic acid encoding the antibody or antigen binding fragment and a host cell harboring the isolated nucleic acid are also provided as are methods for inhibiting Galectin-9-mediated cell signaling in a subject (e.g., a human patient having, suspected of having, or at risk for having, an autoimmune disease, a cancer, or a microbial disease) and treating cancer (e.g., malignant mesothelioma).

DETAILED DESCRIPTION OF THE INVENTION

Figure 1:
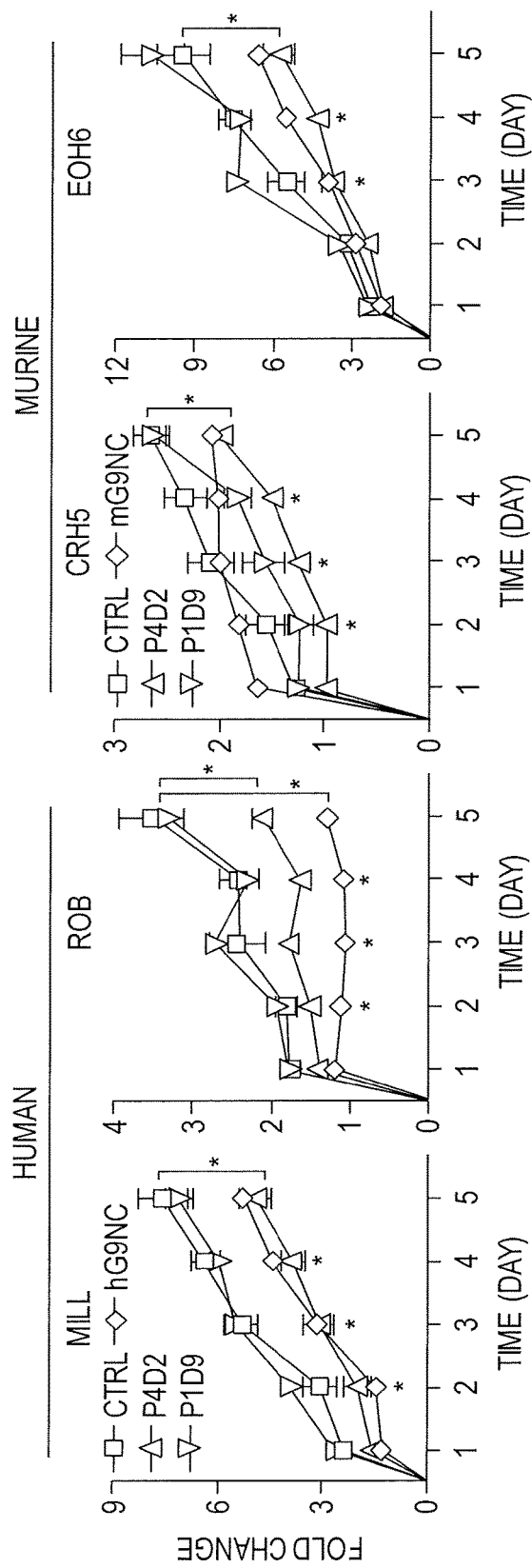
FIG. 1 provides data demonstrating that anti-Galectin-9 P4D2 monoclonal antibody can decrease viability of human malignant mesothelioma cells. Human malignant mesothelioma cells (ROB and MilI) were treated with anti-Galectin-9 monoclonal antibody P4D2 or P1D9, and viability was assessed with an MTT assay. Controls included the human stable recombinant Galectin-9 (hG9NC) and no treatment (Ctrl). Differences between Ctrl and P4D2 as well as Ctrl and hG9NC were statistically significant with P0.01; n=3 (*). A viability assay was also used to evaluate the effects of anti-Galectin-9 P4D2 and P1D9 monoclonal antibodies on mouse malignant mesothelioma cells (CRR5 and EOH6). Mouse stable recombinant Galectin-9 (mG9NC) was included for comparison. Differences between Ctrl and P4D2 as well as Ctrl and mG9NC were statistically significant with P0.01; n=3 (*).

Provided herein is an antibody capable of binding to Galectin-9 (e.g., human, mouse, or both). The novel anti-Galectin-9 antibody of this invention has been found to share unique properties with recombinant Galectin-9 in inducing cancer cell apoptosis and in shifting Tumor Associated Macrophages (TAMs) toward an anti-tumor phenotype. It has been shown that the anti-Galectin-9 antibody, referred to herein as clone P4D2, binds the C-terminal carbohydrate recognition domain (CRD) of Galectin-9, induces cancer cell apoptosis and modulates macrophage polarization in both human and mouse cells. It is important to highlight that treatment with P4D2 monoclonal antibody did not increase cell death. Collectively, the data herein show that the P4D2 antibody can inhibit Galectin-9-mediated cell signaling and is therefore of use in the treatment of cancer and of other Galectin-9-mediated diseases or conditions, e.g., autoimmune and infectious disease. Accordingly, this invention provides an anti-Galectin-9 antibody and methods of using the same to treat Galectin-9-mediated diseases or conditions such as malignant mesothelioma.

As is known in the art, Galectin-9 is an approximately 36-kDa β-d-galactoside mammalian lectin composed of two distinct carbohydrate recognition domains (CRDs) linked by a peptide, which has been shown to have a role in modulating cell-cell and cell-matrix interactions. Several isoforms of Galectin-9 have been identified and the amino acid sequences of these Galectin-9 proteins are known in the art. In particular, human Galectin-9 protein sequences are available under GENBANK Accession Nos. NP_001317092, NP_002299 and NP_0033665 and GenPept Accession No. BAB83624.1 (SEQ ID NO:9); and mouse Galectin-9 protein sequences are available under GENBANK Accession Nos. NP_001152773 and NP_034838 and GenPept Accession No. AAH03754.1 (SEQ ID NO:10).

Galectin-9 is found to interact with Dectin-1, an innate immune receptor which is highly expressed on macrophages in PDA, as well as on cancer cells (Daley, et al. (2017) *Nat. Med.* 23(5):556-6). Regardless of the source of Galectin-9, disruption of its interaction with Dectin-1 has been shown to lead to the reprogramming of $CD4^+$ and $CD8^+$ cells into indispensable mediators of anti-tumor immunity. Thus, Galectin-9 serves as a valuable therapeutic target for blocking the signaling mediated by Dectin-1.

Galectin-9 is also found to interact with TIM-3, a type I cell surface glycoprotein expressed on the surface of leukemic stem cells in all varieties of acute myeloid leukemia (except for M3 (acute promyelocytic leukemia)), but not expressed in normal human hematopoietic stem cells (HSCs). TIM-3 signaling resulting from Galectin-9 ligation has been found to have a pleiotropic effect on immune cells, inducing apoptosis in Th1 cells (Zhu, et al. (2005) *Nat. Immunol.* 6:1245-1252) and stimulating the secretion of tumor necrosis factor-α (TNF-α), leading to the maturation of monocytes into dendritic cells, resulting in inflammation by innate immunity (Kuchroo, et al. (2008) *Nat. Rev. Immunol.* 8:577-580). Further, Galectin-9/TIM-3 signaling has been found to co-activate F-KB and β-catenin signaling, two pathways that promote leukemic stem cells self-renewal (Kikushige, et al. (2015) *Cell Stem Cell* 17(3):341-352). Thus, an anti-Galectin-9 antibody that interferes with Galectin-9/TIM-3 binding could have a therapeutic effect, especially with respect to leukemia and other hematological malignancies.

Galectin-9 is also found to interact with CD206, a mannose receptor highly expressed on M2 polarized macrophages, thereby promoting tumor survival (Enninga, et al. (2018) *J. Pathol.* 245(4):468-477). Tumor-associated macrophages expressing CD206 are mediators of tumor immunosuppression, angiogenesis, metastasis, and relapse (see, e.g., Scodeller, et al. (2017) *Sci. Rep.* 7(1):14655). Specifically, M1 (also termed classically activated macrophages) are trigged by Th1-related cytokines and bacterial products, express high levels of IL-12, and are tumoricidal. By contrast, M2 (so-called alternatively activated macrophages) are activated by Th2-related factors, express high level of anti-inflammatory cytokines, such as IL-10, and facilitate tumor progression (Biswas & Mantovani (2010) *Nat. Immunol.* 11(10):889-96). The pro-tumoral effects of M2 include the promotion of angiogenesis, advancement of invasion and metastasis, and the protection of the tumor cells from chemotherapy-induced apoptosis (Hu, et al. (2015) *Tumour Biol.* 36(12):9119-9126). Tumor-associated macrophages are thought be of M2-like phenotype and have a pro-tumor role. Galectin-9 has been shown to mediate myeloid cell differentiation toward an M2 phenotype (Enninga, et al. (2016) *Melanoma Res.* 26(5):429-41). It is possible that Galectin-9 binding CD206 may result in reprogramming TAMs towards the M2 phenotype, similar to what has been previously shown for Dectin. Without wishing to be bound by theory, blocking the interaction of Galectin-9 with CD206 may provide one mechanism by which an anti-Galectin antibody, e.g., es described herein, can be therapeutically beneficial. Accordingly, in some embodiments, the anti-Galectin-9 antibody described herein may be of use in disrupting the interaction between Galectin-9 and CD206.

Galectin-9 has also been shown to interact with protein disulfide isomerase (PDI) and 4-1BB (Bi, et al. (2011) *Proc. Natl. Acad. Sci. USA* 108(26):10650-5; Madireddi, et al. (2014) *J. Exp. Med.* 211(7):1433-48). As such, an anti-Galectin-9 antibody described herein may be of use in disrupting the interaction between Galectin-9 and PDI and/or 4-1BB.

For the purposes of this invention, a "Galectin-9 antibody" or "anti-Galectin-9 antibody" refers to an antibody that binds to one or more Galectin-9 proteins. The term "Galectin-9 antibody" or "anti-Galectin-9 antibody" refers to any antibody capable of binding to a Galectin-9 polypeptide, which can be of a suitable source, for example, human or a non-human mammal (e.g., mouse, rat, rabbit, primate such as monkey, etc.). In some embodiments, the anti-Galectin-9 antibody can be used therapeutically to suppress the bioactivity of Galectin-9. In some embodiments, the anti-Galectin-9 antibody may be used in research or may be used in diagnostic/prognostic methods, e.g., for the detection of cells expressing Galectin-9 in an assessment of treatment eligibility and/or efficacy.

As used herein, the term "antibody," e.g., anti-Galectin-9 antibody, encompasses not only intact (e.g., full-length) polyclonal or monoclonal antibodies, but also antigen-binding fragments thereof (such as Fab, Fab', F(ab')2, Fv), single chain (scFv), mutants thereof, fusion proteins including an antibody portion, humanized antibodies, chimeric antibodies, diabodies, nanobodies, linear antibodies, single chain antibodies, multispecific antibodies (e.g., bispecific antibodies) and any other modified configuration of the immunoglobulin molecule that includes an antigen recognition site of the required specificity, including glycosylation variants of antibodies, amino acid sequence variants of antibodies, and covalently modified antibodies. An antibody, e.g., anti-Galectin-9 antibody, includes an antibody of any class, such as IgD, IgE, IgG, IgA, or IgM (or sub-class thereof), and the antibody need not be of any particular class. In certain embodiments of this invention, the heavy chain constant region of the anti-Galectin-9 antibody is from a human IgG (a gamma heavy chain) of any IgG subfamily as described herein, e.g., IgG2. Further, the anti-Galectin-9 antibody provided herein may comprise a heavy chain variable region framework of VH 9-3; and/or a light chain variable region framework of VK 8-21.

A typical antibody molecule comprises a heavy chain variable region (VH) and a light chain variable region (VL), which are usually involved in antigen binding. The VH and VL regions can be further subdivided into regions of hypervariability, also known as "complementarity determining regions" ("CDRs"), interspersed with regions that are more conserved, which are known as "framework regions" ("FR"). Each VH and VL is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, and/or the contact definition, all of which are well known in the art. See, e.g., Kabat, et al. (1991) Sequences of Proteins of Immunological Interest, Fifth Edition, U.S. Department of Health and Human Services, NIH Publication No. 91-3242; Chothia, et al. (1989) Nature 342:877; Chothia, et al. (1987) J. Mol. Biol. 196:901-917, Al-lazikani, et al. (1997) J. Molec. Biol. 273:927-948; and Almagro (2004) J. Mol. Recognit. 17:132-143.

The anti-Galectin-9 antibody described herein may be a full-length antibody, which contains two heavy chains and two light chains, each including a variable domain and a constant domain. Alternatively, the anti-Galectin-9 antibody can be an antigen-binding fragment of a full-length antibody. Examples of binding fragments encompassed within the term "antigen-binding fragment" of a full length antibody include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward, et al. (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird, et al. (1988) Science 242:423-426; and Huston, et al. (1988) Proc. Natl. Acad. Sci. USA 85:5879-5883.

The anti-Galectin-9 antibody as described herein, i.e., P4D2, can bind and inhibit (e.g., reduce or eliminate) the activity of Galectin-9. In some embodiments, the anti-Galectin-9 antibody as described herein can bind and inhibit the activity of Galectin-9 by at least 30% (e.g., 31%, 35%, 40%, 45%, 50%, 60%, 70%, 80%, 90%, 95% or greater, including any increment therein). The inhibitory activity of an anti-Galectin-9 antibody described herein can be determined by routine methods known in the art.

In some embodiments, the anti-Galectin-9 antibody promotes cell apoptosis in target cells expressing Galectin-9, e.g., cancer cells or immune suppressive immune cells. In some embodiments, the anti-Galectin-9 antibody induces apoptosis in cancer cells by at least 30% (e.g., 31%, 35%, 40%, 50%, 60%, 70%, 80%, 90%, 95% or greater, including any increment therein). Such inhibitory activity can be determined by conventional methods or the assays described herein.

In other embodiments, the anti-Galectin-9 antibody promotes polarization of tumor macrophages toward M1-like myeloid cells. In some embodiments, the anti-Galectin-9 antibody increases polarization of target macrophages by at least 30% (e.g., 31%, 35%, 40%, 50%, 60%, 70%, 80%, 90%, 95% or greater, including any increment therein). Polarization toward an M1 phenotype can be determined by, e.g., determining the production of the anti-tumor enzyme, iNOS.

The antibody described herein can be murine, rat, human, or any other origin (including chimeric or humanized antibodies). Such antibodies are non-naturally occurring, i.e., would not be produced in an animal without human act (e.g., immunizing such an animal with a desired antigen or fragment thereof or isolated from antibody libraries). Further, the anti-Galectin-9 antibody can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In some embodiments, the anti-Galectin-9 antibody is a humanized antibody. In some embodiments, the anti-Galectin-9 antibody is a humanized antibody having one of more of the elements or characteristics described below or elsewhere herein. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. In general, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may include residues that are found neither in the recipient antibody nor in the imported CDR or framework sequences, but are included to further refine and optimize antibody performance. In some instances, the humanized antibody may include substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will include at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, or six) which are altered with respect to the original antibody, which are also termed one or more CDRs "derived from" one or more CDRs from the original antibody. Humanized antibodies may also involve affinity maturation.

Methods for constructing humanized antibodies are also well known in the art. See, e.g., Queen, et al. (1989) *Proc. Natl. Acad. Sci. USA* 86:10029-10033. In one example, variable regions of VH and VL of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human VH and VL chains having amino acid sequences that are homologous to those of the parent non-human antibody are identified from any antibody gene database using the parent VH and VL sequences as search queries. Human VH and VL acceptor genes are then selected. The CDR regions within the selected human acceptor genes can be replaced with the CDR regions from the parent non-human antibody or functional variants thereof. When necessary, residues within the framework regions of the parent chain that are predicted to be important in interacting with the CDR regions can be used to substitute for the corresponding residues in the human acceptor genes.

In some embodiments, the anti-Galectin-9 antibody is a chimeric antibody. In some embodiments, the anti-Galectin-9 antibody is a chimeric antibody which may include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region. In some embodiments, the anti-Galectin-9 antibody described herein specifically binds to the corresponding target antigen or an epitope thereof, e.g., Galectin-9 antigen or epitope. An antibody that "specifically binds" to an antigen or an epitope is a term well understood in the art. A molecule is said to exhibit "specific binding" if it reacts more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to an antigen (Galectin-9) or an antigenic epitope therein is an antibody that binds this target antigen with greater affinity, avidity, more readily, and/or with greater duration than it binds to other antigens or other epitopes in the same antigen. It is also understood with this definition that, for example, an antibody that specifically binds to a first target antigen may or may not specifically or preferentially bind to a second target antigen. As such, "specific binding" or "preferential binding" does not necessarily require (although it can include) exclusive binding. In some examples, an antibody that "specifically binds" to a target antigen or an epitope thereof may not bind to other antigens or other epitopes in the same antigen (i.e., only baseline binding activity can be detected in a conventional method). In some embodiments, the anti-Galectin-9 antibody described herein specifically binds to Galectin-9. In some embodiments, the anti-Galectin-9 antibody described herein specifically binds to the C-terminal CRD of Galectin-9. In particular embodiments, the anti-Galectin-9 antibody interacts or binds to one or more of amino acid residues 204-205, 228-232, 250-254, 256-257, 259, 281-283 and 298-306 of Galectin-9 (SEQ ID NO:9).

In some aspects, the anti-Galectin-9 antibody, or antigen binding fragment thereof, has a variable heavy chain region (VH) sequence comprising SEQ ID NO:NO:7 or consisting of SEQ ID NO:7. In other aspects, the anti-Galectin-9 antibody, or antigen binding fragment thereof, has a variable light chain region (VL) sequence comprising SEQ ID NO:NO:8 or consisting of SEQ ID NO:8. In certain embodiments, the anti-Galectin-9 antibody, or antigen binding fragment thereof, has a VH sequence comprising SEQ ID NO:7 and a VL sequence comprising SEQ ID NO:8. In further embodiments, the anti-Galectin-9 antibody, or antigen binding fragment thereof, has a VH sequence consisting essentially of SEQ ID NO:7 and a VL sequence consisting essentially of SEQ ID NO:8. In still other embodiments, the anti-Galectin-9 antibody, or antigen binding fragment thereof, has a VH sequence consisting of SEQ ID NO:7 and a VL sequence consisting of SEQ ID NO:8.

In some examples, the anti-Galectin-9 antibody, or antigen binding fragment thereof, may include the same heavy chain and the same light chain sequence as the reference antibody, i.e., the P4D2 monoclonal antibody provided herein. In particular, the anti-Galectin-9 antibody, or antigen binding fragment thereof, has a heavy chain, which is at least 90% (e.g., 90%, 91%, 92%, 93%, 94%, 95%, 96%, 97%, 98%, or 99%) identical to SEQ ID NO:7. Further, the anti-Galectin-9 antibody, or antigen binding fragment thereof, may include a light chain, which is at least 90% (e.g., 90%, 91%, 92%, 93%, 94%, 95%, 96%, 97%, 98%, or 99%) identical to SEQ ID NO:8. Ideally, the anti-Galectin-9 antibody, or antigen binding fragment thereof, has a heavy chain and a light chain, which collectively are at least 90% (e.g., 90%, 91%, 92%, 93%, 94%, 95%, 96%, 97%, 98%, or 99%) identical to the heavy chain and light chain sequences of the reference antibody, i.e., the P4D2 monoclonal antibody provided herein. In particular embodiments, the isolated anti-Galectin 9 antibody, or antigen binding fragment thereof, has heavy and light chain variable regions, wherein the heavy chain variable region has an amino acid sequence of SEQ ID NO:7 and a light chain variable region has an amino acid sequence of SEQ ID NO:8.

In certain aspects, the anti-Galectin-9 antibody of this invention may include the same heavy chain complementarity determining regions (CDRs) and the same light chain CDRs as the reference antibody, i.e., the P4D2 monoclonal antibody provided herein. In particular, the anti-Galectin-9 antibody has a heavy chain complementarity determining region 1 (CDR1), a heavy chain complementary determining region 2 (CDR2), and a heavy chain complementary determining region 3 (CDR3), which collectively are at least 90% (e.g., 90%, 91%, 92%, 93%, 94%, 95%, 96%, 97%, 98%, or 99%) identical to the heavy chain CDRs of the P4D2 monoclonal antibody. In some embodiments, the anti-Galectin-9 antibody includes a light chain CDR1, a light chain CDR2, and a light chain CDR3, which collectively are at least 90% (e.g., 90%, 91%, 92%, 93%, 94%, 95%, 96%, 97%, 98%, or 99%) identical to the light chain CDRs of the P4D2 monoclonal antibody.

In some aspects, the anti-Galectin-9 antibody, or antigen binding fragment thereof, has heavy and light chain variable regions with one or more of the following CDR amino acid sequences: (a) VH CDR1 amino acid sequence of GYTFTNFG (SEQ ID NO:1); (b) VH CDR2 amino acid sequence of INTYKGVP (SEQ ID NO:2); (c) VH CDR3 amino acid sequence of ARRKDGDDYYAMDY (SEQ ID NO:3); (d) VL CDR1 amino acid sequence of QSLFNSRT (SEQ ID NO:4); (e) VL CDR2 amino acid sequence of WAS (SEQ ID NO:5); and (f) VL CDR3 amino acid sequence of KQSYNQWT (SEQ ID NO:6).

According to certain aspects, the anti-Galectin-9 antibody, or antigen binding fragment thereof, comprises a (a) VH CDR1 amino acid sequence of GYTFTNFG (SEQ ID NO:1); (b) VH CDR2 amino acid sequence of INTYKGVP (SEQ ID NO:2); (c) VH CDR3 amino acid sequence of ARRKDGDDYYAMDY (SEQ ID NO:3); (d) VL CDR1 amino acid sequence of QSLFNSRT (SEQ ID NO:4); (e) VL CDR2 amino acid sequence of WAS (SEQ ID NO:5); and (f) VL CDR3 amino acid sequence of KQSYNQWT (SEQ ID NO:6). In some embodiments, the light and heavy chain variable region CDR1, CDR2, and CDR3 regions consist of SEQ ID NO:1, SEQ ID NO:2 and SEQ ID NO:3, respectively, and SEQ ID NO:4, SEQ ID NO:5 and SEQ ID NO:6, respectively.

Because Galectin-9 binding specificity is dictated essentially by the CDR1, CDR2 and CDR3 regions of the antibody, the VH CDR1, CDR2 and CDR3 sequences and the VL CDR1, CDR2 and CDR3 sequences disclosed above, can be mixed and matched to generate new Galectin-9 binding antibodies, as long as each resulting new antibody has a VL CDR1, CDR2 and CDR3 and a VH CDR1, CDR2 and CDR3. Such antibodies resulting from a new combination of CDRs described herein can be tested using the binding assays described herein. In some embodiments, the CDR1, CDR2 and/or CDR3 sequence from a particular VH or VL sequence is replaced with a structurally similar CDR sequence(s). Novel VH and VL sequences can be created by substituting one or more VH and/or VL CDR sequence(s) with structurally similar sequences according to methods known in the art.

Accordingly, also within the scope of the present disclosure are functional variants of the exemplary anti-Galectin-9 antibody as disclosed herein. Such functional variants are substantially similar to the exemplary antibody, both structurally and functionally. A functional variant comprises substantially the same VH and VL CDRs as the exemplary antibody. For example, it may comprise only up to 5 (e.g., 4, 3, 2, or 1) amino acid residue variations in the total CDR regions of the antibody and binds the same epitope of Galectin-9 with substantially similar affinity (e.g., having a $K_D$ value in the same order). Alternatively, or in addition, the amino acid residue variations are conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, Sambrook, et al., eds., Second Edition, Cold Spring Harbor Laboratory Press, Cold Spring Harbor, New York (1989); or *Current Protocols in Molecular Biology*, Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

The "percent identity" of two amino acid sequences is determined using the algorithm of Karlin & Altschul (1990) *Proc. Natl. Acad. Sci. USA* 87:2264-68, modified as in Karlin & Altschul (1993) *Proc. Natl. Acad. Sci. USA* 90:5873-77. Such an algorithm is incorporated into the NBLAST and XBLAST programs (version 2.0) of Altschul, et al. (1990) *J. Mol. Biol.* 215:403-10. BLAST protein searches can be performed with the XBLAST program, score=50, wordlength=3 to obtain amino acid sequences homologous to the protein molecules of interest.

In addition of the variable regions disclosed herein, the antibody of this invention may include a heavy chain constant region (CH) or a portion thereof (e.g., CH1, CH2, CH3, or a combination thereof) and/or light chain constant region (CL) or a portion thereof (e.g., CL1, CL2, CL3, or a combination thereof). The constant regions can be of any suitable origin, e.g., human, mouse, rat, or rabbit. In one specific example, the constant region sequences are from a human IgG of any IgG subfamily. In some embodiments, the anti-Galectin-9 antibody includes a modified constant region. In some embodiments, the anti-Galectin-9 antibody includes a modified constant region that is immunologically inert, e.g., does not trigger complement mediated lysis, or does not stimulate antibody-dependent cell-mediated cytotoxicity (ADCC). ADCC activity can be assessed using methods disclosed in U.S. Pat. No. 5,500,362.

An anti-Galectin-9 antibody capable of binding Galectin-9 as described herein can be made by any method known in the art. See, for example, Harlow & Lane (1998) *Antibodies: A Laboratory Manual*, Cold Spring Harbor Laboratory, New York. In some embodiments, antibodies specific to a target antigen (e.g., Galectin-9 or a CRD thereof) are made by conventional hybridoma technology. If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. Accordingly, certain aspects of this invention include nucleic acids encoding an anti-Galectin-9 antibody, or antigen binding fragment thereof, as well as vectors and host cells harboring such nucleic acids. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the activity of Galectin-9. It will be apparent to one of skill in the art that one or more polynucleotide changes can be made to the antibody and still maintain its binding specificity to the target antigen.

In alternate embodiments, antibodies capable of binding to the target antigens as described herein are isolated from a suitable antibody library, including phage display, yeast display, ribosomal display, or mammalian display technology.

After selecting candidate library members that bind to a target, each candidate library member can be further analyzed, e.g., to further characterize its binding properties for the target, e.g., Galectin-9. Each candidate library member can be subjected to one or more secondary screening assays. The assay can be for a binding property, a catalytic property, an inhibitory property, a physiological property (e.g., cytotoxicity, renal clearance, immunogenicity), a structural property (e.g., stability, conformation, oligomerization state) or another functional property. The same assay can be used repeatedly, but with varying conditions, e.g., to determine pH, ionic, or thermal sensitivities.

As appropriate, the assays can use a display library member directly, a recombinant polypeptide produced from the nucleic acid encoding the selected polypeptide, or a synthetic peptide synthesized based on the sequence of the selected polypeptide. In the case of selected Fabs, the Fabs can be evaluated or can be modified and produced as intact IgG proteins. Once produced, an antibody with specificity for Galectin-9 can be isolated. Exemplary methods for isolating antibodies include, but are not limited to, affinity chromatography with a Protein A or Protein G coupled matrix.

The present disclosure further provides pharmaceutical compositions including the anti-Galectin-9 antibody described herein, or antigen binding fragment thereof, and use of the same in methods for inhibiting or reducing signaling mediated by Galectin-9 and/or treating a Galectin-9-mediated disease. The anti-Galectin-9 antibody or antigen binding fragment thereof (as well as the encoding nucleic acids or nucleic acid sets, vectors comprising such, or host cells comprising the vectors) can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., *Remington: The Science and Practice of Pharmacy* 20th Ed. (2000) Lippincott Williams and Wilkins, Ed. K. E. Hoover.

The pharmaceutical compositions to be used in the present methods can include pharmaceutically acceptable carriers, excipients, or stabilizers in the form of lyophilized formulations or aqueous solutions. Acceptable carriers, excipients, or stabilizers are nontoxic to recipients at the dosages and concentrations used, and may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as poloxamers or polyethylene glycol (PEG). In some examples, the pharmaceutical composition described herein includes liposomes containing the antibody (or the encoding nucleic acids) which can be prepared by methods known in the art, such as described in Epstein, et al. (1985) *Proc. Natl. Acad. Sci. USA* 82:3688; Hwang, et al. (1980) *Proc. Natl. Acad. Sci. USA* 77:4030; U.S. Pat. Nos. 4,485,045 and 4,544,545. Liposomes with enhanced circulation time are disclosed in U.S. Pat. No. 5,013,556. Particularly useful liposomes can be generated by the reverse-phase evaporation method with a lipid composition including phosphatidylcholine, cholesterol and PEG-derivatized phosphatidylethanolamine (PEG-PE). Liposomes are extruded through filters of defined pore size to yield liposomes with the desired diameter.

The anti-Galectin-9 antibody, or the encoding nucleic acid(s), may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., *Remington, The Science and Practice of Pharmacy* 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as lactic acid-glycolic acid copolymer and leuprolide acetate, sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of an antibody of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the composition can be coated or otherwise compounded to provide a dosage form affording the advantage of prolonged action. For example, the tablet or pill can include an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate. Suitable surface-active agents include, in particular, non-ionic agents, such as polyoxyethylenesorbitans and other sorbitans. Compositions with a surface-active agent will conveniently include between 0.05% and 5% surface-active agent, and can be between 0.1% and 2.5%. It will be appreciated that other ingredients may be added, for example mannitol or other pharmaceutically acceptable vehicles, if necessary.

Suitable emulsions may be prepared using commercially available fat emulsions, such as those sold under the trademarks INTRALIPID®, LIPOSYN®, and LIPOFUNDIN®. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5% and 20%. The fat emulsion can include fat droplets between 0.1 µm and 1.0 µm, particularly 0.1 µm and 0.5 µm, and have a pH in the range of 5.5 to 8.0. By way of illustration, emulsion compositions can be those prepared by mixing an antibody with INTRALIPID® or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

In some embodiments, compositions of the disclosure may include an anti-Galectin-9 antibody by itself, or such compositions may include an anti-Galectin-9 antibody in combination with one or more prophylactic agents, therapeutic agents (e.g., chemotherapy or immunotherapy), and/or pharmaceutically acceptable carriers. In certain aspects, the compositions and methods of this invention include the use of an anti-Galectin-9 antibody in combination with one or more of a checkpoint inhibitor molecule and/or a co-stimulatory molecule. In certain embodiments, the checkpoint inhibitor molecule is selected from the group of PD-1, PD-L1, PD-L2, CTLA-4, LAG3, TIM-3, TIGIT and A2aR. In other embodiments, the co-stimulatory molecule is selected from the group of OX40, GITR, CD137, CD40, CD27, and ICOS. In some embodiments, the methods are provided, wherein the anti-Galectin-9 antibody is administered concurrently with a checkpoint inhibitor. In some embodiments, the anti-Galectin-9 antibody is administered before or after a checkpoint inhibitor. In some embodiments, the checkpoint inhibitor is administered systemically. In some embodiments, the checkpoint inhibitor is administered locally.

As indicated, the invention provides methods for inhibiting or reducing signaling mediated by Galectin-9 and in the treatment of a Galectin-9-mediated disease. In accordance with these methods, a subject in need of treatment is administered an effective amount of the anti-Galectin antibody of this invention or pharmaceutical composition containing the same to reduce, ameliorate, or eliminate a Galectin-9-mediated disease or condition.

To practice the methods disclosed herein, an effective amount of the antibody or pharmaceutical composition described herein can be administered to a subject {e.g., a human) in need of the treatment via a suitable route, systemically or locally. In some embodiments, the anti-Galectin-9 antibody is administered by intravenous administration, e.g., as a bolus or by continuous infusion over a period of time, by intramuscular, intraperitoneal, intracerebrospinal, subcutaneous, intra-arterial, intra-articular, intra-synovial, intrathecal, intratumoral, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibody as described herein can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a target disease/disorder, such as a cancer, autoimmune disease (such as an allergic disorder), or microbial disease. Examples of cancers that can be treated in accordance with this invention include, but are not limited to, adrenal cancer, adrenocortical carcinoma, anal cancer, appendix cancer, bile duct cancer, bladder cancer, bone cancer, brain cancer, central nervous system tumors, breast cancer, Castleman disease, cervical cancer, colon cancer, rectal cancer, colorectal cancer, endometrial cancer, esophageal cancer, eye cancer, gallbladder cancer, gastrointestinal cancer, gastrointestinal carcinoid tumors, gastrointestinal stromal tumors, genitourinary cancers, gestational trophoblastic disease, heart cancer, Kaposi sarcoma, kidney cancer, laryngeal cancer, hypopharyngeal cancer, leukemia, liver cancer, lung cancer (for example, non-small cell lung cancer, NSCLC, and small cell lung cancer, SCLC), lymphoma, malignant mesothelioma, multiple myeloma, myelodysplastic syndrome, nasal cavity cancer, paranasal sinus cancer, pancreatic duct adenocarcinoma (PDA) nasopharyngeal cancer, neuroblastoma, oral cavity cancer, oropharyngeal cancer, osteosarcoma, ovarian cancer, pancreatic cancer, penile cancer, pituitary tumors, prostate cancer, retinoblastoma, rhabdomyosarcoma, rhabdoid tumor, salivary gland cancer, sarcoma, skin cancer, squamous cell head and neck cancer, small intestine cancer, stomach cancer, teratoid tumor, testicular cancer, throat cancer, thymus cancer, thyroid cancer, unusual childhood cancers, upper and lower gastrointestinal malignancies, urethral cancer, uterine cancer, uterine sarcoma, vaginal cancer, vulvar cancer, Waldenstrom macroglobulinemia, and Wilms tumor. A subject having cancer can be identified by routine medical examination, e.g., laboratory tests, organ functional tests, CT scans, or ultrasounds. In certain embodiments, the cancer is malignant mesothelioma.

Examples of autoimmune diseases include rheumatoid conditions, metabolic and endocrine conditions, as well as respiratory and allergic conditions. A subject having an autoimmune disease can be identified by routine medical examination, e.g., with laboratory tests, such as antinuclear antibodies, anti-mitochondrial autoantibodies, anti-neutrophil cytoplasmic antibody, anti-phospholipid antibodies, anti-citrullinated peptide (anti-CCP), anti-rheumatoid factor, immunoglobulin A, C-reactive protein test, complement test, erythrocyte sedimentation rate (ESR) test, blood clotting profile, and protein electrophoresis/immunofixation electrophoresis, among others.

Microbial diseases can be caused by a variety of pathogens, including bacteria, fungi, protozoa and viruses. Exemplary infectious bacteria include, e.g., *Streptococcus* ssp., *Neisseria gonorrheae*, *Clostridium* spp., *Hemophilus influenzae*, *Klebsiella pneumoniae*, *Staphylococcus aureus*, *Vibrio colerae*, *Escherichia coli*, *Pseudomonas aeruginosa*, *Bacillus aereus*, *Yersinia pestis*, *Salmonella typhimurium*, *Mycobacterium tuberculosis*, and *Mycoplasma* spp. Examples of pathologic fungi include *Aspergillus fumigatus*, *Candida albicans*, *Blastomyces dermatitidis*, *Cryptococcus neoformans*, and *Histoplasma capsulatum*. Pathologic protozoa include *Entamoeba histolytica*, *Toxoplasma gondii*, *Trichomonas* spp, *Tryoanosoma* spp., *Pneumocystis* pneumonia, *Plasmodium falciparum*, and *Plasmodium* malaria. Viral infectious diseases include those caused by Adenovirus, Hantavirus, Ebola virus, Marburg Virus, Dengue virus, Yellow fever virus, Hepatitis virus, Herpes simplex virus, Cytomegalovirus, Epstein Barr virus, Varicella Zoster Virus, Human Herpesvirus, Influenza virus, Rubella virus, Mumps virus, Measles virus, Respiratory Syncytial virus, Papillomaviruses, Parvovirus, Coxsackie virus, Polioviruses, Rhinoviruses, Rabies Virus, Human Immunodeficiency virus, and Human T-cell Leukemia virus. A subject having a microbial disease can be identified by routine medical examination, e.g., laboratory tests. For example, microscopy (e.g., Gram-positive and/or Gram-negative staining), sample culturing, biochemical tests (e.g., tests for metabolic and/or enzymatic products, such as fermentation products, acids, alcohol, or gases), and molecular diagnostics (e.g., PCR) may be used.

A subject suspected of having any of such target disease/disorder might show one or more symptoms of the disease/disorder. A subject at risk for the disease/disorder can be a subject having one or more of the risk factors for that disease/disorder. By way of illustration, a subject suspected of having malignant mesothelioma may exhibit one or more of the following symptoms: dry cough or wheezing, shortness of breath (dyspnea), respiratory complications, pain in the chest or abdomen, fever or night sweats, pleural effusion, fatigue and muscle weakness.

As used herein, "an effective amount" refers to the amount of each active agent required to confer therapeutic effect on the subject, either alone or in combination with one or more other active agents. In some embodiments, the therapeutic effect is reduced Galectin-9 activity or increased anti-tumor immune responses in the tumor microenvironment. Non-limiting examples of increased anti-tumor responses include increased apoptosis of cancer cells or immune suppressive immune cells, or switching of the TAMs from the M2 to the Ml phenotype. Determination of whether an amount of the antibody achieves the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a target disease/disorder. Alternatively, sustained continuous release formulations of an antibody may be appropriate. Various formulations and devices for achieving sustained release are known in the art. In one example, dosages for an antibody as described herein may be determined empirically in individuals who have been given one or more administration(s) of the antibody. Individuals are given incremental dosages of the antagonist. To assess efficacy of the antagonist, an indicator of the disease/disorder can be followed.

Generally, for administration of the antibody described herein, an initial candidate dosage can be about mg/kg. For the purpose of the present disclosure, a typical daily dosage might range from about 0.1 µg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen can vary over time.

As used herein, the term "treating" refers to the application or administration of a composition including one or more active agents to a subject, who has a target disease or disorder, a symptom of the disease/disorder, or a predisposition toward the disease/disorder, with the purpose to delay, cure, heal, alleviate, relieve, alter, remedy, ameliorate, improve, or affect the disorder, the symptom of the disease, or the predisposition toward the disease or disorder.

Ideally, the methods of the present disclosure provide anti-tumor activity (e.g., reduce cell proliferation, tumor growth, tumor volume, and/or tumor burden or load or reduce the number of metastatic lesions over time) by at least about 10%, 20%, 25%, 30%, 40%, 50%, 60%, 70%, 75%, 80%, 85%, 90%, 95%, or more as compared to levels prior to treatment or in a control subject. In some embodiments, reduction is measured by comparing cell proliferation, tumor growth, and/or tumor volume in a subject before and after administration of the pharmaceutical composition. In some embodiments, the method of treating or ameliorating a cancer in a subject allows one or more symptoms of the cancer to improve by at least about 10%, 20%, 30%, 40%, 50%, 60%, 70%, 80%, 90%, 95%, or more. Before, during, and after the administration of the pharmaceutical composition, cancerous cells and/or biomarkers in a subject may be measured in a biological sample, such as blood, serum, plasma, urine, peritoneal fluid, and/or a biopsy from a tissue or organ. In some embodiments, the methods may include administration of the compositions of the invention to reduce tumor volume, size, load or burden in a subject to an undetectable size, or to less than about 1%, 2%, 5%, 10%, 20%, 25%, 30%, 40%, 50%, 60%, 70%, 75%, 80%, or 90% of the subject's tumor volume, size, load or burden prior to treatment. In other embodiments, the methods may include administration of the compositions of the invention to reduce the cell proliferation rate or tumor growth rate in a subject to an undetectable rate, or to less than about 1%, 2%, 5%, 10%, 20%, 25%, 30%, 40%, 50%, 60%, 70%, 75%, 80%, or 90% of the rate prior to treatment. In other embodiments, the methods may include administration of the compositions of the invention to reduce the development of or the number or size of metastatic lesions in a subject to an undetectable rate, or to less than about 1%, 2%, 5%, 10%, 20%, 25%, 30%, 40%, 50%, 60%, 70%, 75%, 80%, or 90% of the rate prior to treatment. In particular embodiments, administering the composition has a positive impact on overall survival. In some embodiments, the disclosure provides the use of an anti-Galectin-9 antibody as a medicament for the treatment of cancer, wherein the anti-Galectin-9 antibody is P4D2, and wherein the cancer is malignant mesothelioma.

The following non-limiting examples are provided to further illustrate the present invention.

Example 1: Materials and Methods

Immunohistochemistry (IHC). IHC was performed on formalin-fixed paraffin-embedded tissue sections from human malignant mesothelioma tumor biopsies and normal human peritoneal mesothelial lining. Assessment of tumor content was based on hematoxylin-eosin stained sections, combined with immunohistochemical features (Wilm Tumor-1, Calretinin, Cytokeratin 5/6 stains). Expert pathologists in pleural pathology, independently evaluated the biopsies. Standard immunohistochemistry for Galectin-9 (LS-136275 monoclonal antibody, LSBio, Seattle WA) was performed by conventional methods, using the avidin-biotin-peroxidase complex method in a DAKO-autostainer (Carpinteria, CA). Slides were counterstained with hematoxylin to visualize nuclei and mounted using Tissue-Mount mounting medium (VWR; Radnor, PA). Expression of Galectin-9 was analyzed with an Olympus BX43 microscope. Presence of Galectin-9-positive tumor cells was evaluated on 10 fields per slide at 200× original magnification.

Mice. Female BALE/c mice, 6-8 weeks of age, were purchased from Jackson Laboratory. Galectin-9 knockout (KO) female BALB/c mice were provided by GalPharma, Co., Ltd., (Kagawa, Japan). All mice were maintained in a specific pathogen-free animal facility for at least 1 week before each experiment.

Recombinant Proteins. Recombinant human Galectin-1, -3, -4, -7, -8, stable Galectin-9 (hG9NC) and mouse stable Galectin-9 (mG9NC) were obtained from GalPharma (Takamatsu; Kagawa, Japan). Stable Galectin-9 is an artificial form of Galectin-9 that lacks the fragile linker peptide of Galectin-9 in order to give stability to the protein (Nishi, et al. (2005) *FEBS Lett* 579:2058-2064). Human stable galecin-9 is composed of N- and C-terminal carbohydrate-recognition domains (CRDs) linked by His-Met residues, where N-CRD and C-CRD respectively correspond to amino acid residues 1-148 and 178-323 of Galectin-9 as available under GenPept accession number BAB83624.1. Mouse stable Galectin-9 is composed of N-CRD and C-CRD linked by Gly-Ser residues where N-CRD and C-CRD respectively correspond to amino acid residues 1-147 and 177-322 of mouse Galectin-9 available under GenPept accession number AAH03754.1. hG8G9 and hG9G8 are artificial constructs generated by swapping the N-CRD and C-CRD of Galectin-8 and -9. Briefly, the open reading frames of hG9NC and hG8NC in a pET11a vector were digested by NdeI to excise DNA fragments coding for N-CRDs of human Galectin-8 and human Galectin-9, respectively. The excised DNA fragments were then ligated with the rest of the DNA fragments in alternate combinations. All the recombinant Galectins were expressed by *E. coli* BL21 (DE3), purified with lactose-Cellufine™ (Chisso; Tokyo, Japan) and made endotoxin-free using Cellufine™ ETclean (Chisso). Recombinant wild-type Galectin-9 was purchased from R&D Systems (Minneapolis, MN).

Production of Anti-Galectin-9 Monoclonal Antibodies. Four Galectin-9 KO female BALE/c mice (4-6 weeks old) were immunized with recombinant human stable Galectin-9 (hG9NC) and four with recombinant murine stable Galectin-9 (mG9NC). Both hG9NC and mG9NC were stabilized by removing the peptide linker between N-CRD and C-CRD described herein. Immunizations (25 µg of protein) were administered intraperitoneally (i.p.) at days 0, 16, 31, and 54 with aluminum hydroxide (alum) adjuvant. An enzyme-linked immunosorbent assay (ELISA) was performed on mouse sera to determine hG9NC and mG9NC reactivity, with pre-immunization sera used as a negative control. The mouse responding best to human and murine Galectin-9 was boosted for five days, then sacrificed and its splenocytes fused with P3X63Ag8.653 cells at a ratio of 5:1 according to previously described methods (Kohler & Milstein (1992) *Biotechnology* 24:524-526). Ten days post-fusion, hybridoma supernatants were assessed via ELISA for binding to hG9NC and mG9NC. Hybridomas of interest were subcloned twice and expanded. High-binding 96-well microtiter plates (Corning) were coated with either hG9NC or mG9NC at a concentration of 100 ng/well in phosphate-buffered saline (PBS) overnight at 4° C. After washing with borate-buffered saline (BBS), the wells were blocked with BBS containing 5% non-fat milk powder for 30 minutes. Either mouse sera diluted in 2.5% non-fat milk powder/BBS or raw hybridoma supernatant were added to wells at room temperature for 1 hour. After a washing step with BBS, the anti-Galectin-9 monoclonal antibody amount was ascertained using alkaline phosphatase-coupled (AP) goat anti-mouse IgG (H+L) (SouthernBiotech) and p-Nitrophenyl Phosphate (PNPP) (Pierce). Microtiter plates were incubated for 30 minutes and then the optical density was read at 405 nm using a Synergy HI Microplate Reader (BioTek Instruments).

Purification and Titration of Antibodies. Hybridomas were grown in Dulbecco's Modified Eagle's Medium (DMEM) containing 10% ultra-low IgG fetal bovine serum (FBS)(Life Technologies) and the supernatants were collected and diluted (at a ratio of 1:1) with PBS. Purification was carried out by chromatography on a Protein G-gel filtration columns (HiTrap™ Protein G HP; GE Healthcare) according to the manufacturer's recommendations and purity was confirmed by SDS-PAGE under reducing conditions. Purified monoclonal antibodies were subsequently dialyzed and concentrated against 0.05 mM PBS, pH 7.4. The monoclonal antibodies were tested and found to be endotoxin free (<0.01 Endotoxin Units (EU)/mg) using the limulus amebocyte lysate (LAL) assay.

Protein concentrations of the purified monoclonal antibodies were ascertained via the bicinchoninic acid (BCA) protein assay (Pierce, Thermoscientific) and were then adjusted to 2 mg/ml. The titer of the monoclonal antibodies was determined by ELISA as described above, using 100 µl of continuous dilution (two-fold serial dilutions starting from 1:100) of purified monoclonal antibody.

Determination of Monoclonal Antibody Isotype and Cross-Reactivity. The class and subclass of the monoclonal antibodies were determined using an Ig Isotyping mouse ELISA (Invitrogen). The monoclonal antibodies were also tested for cross-reactivity with other members of the Galectin family by ELISA as above described, using 96-well plates coated with 100 ng/well of Galectin-1, -3, -4, -7, -8, or -9. Human recombinant Galectin-9 (hrGal9) (R&D Systems) was used as a control. Monoclonal antibody reactivity to the following two fusion proteins was also measured: hG9G8 composed of a human Galectin-9 N-terminus and human Galectin-8C terminus; and hG8G9 composed of a human Galectin-8 N-terminus and human Galectin-9 C-terminus. These fusion proteins were provided by GalPharma (Takamatsu; Kagawa, Japan).

Anti-Galectin-9 P4D2 Monoclonal Antibody Fv Sequencing and Galectin-9 Modeling. RNA was extracted from the P4D2 Hybridomas using a chemical reagent for isolating biological material from organic tissue sold under the trademark TRIZOL® (ThermoFisher Scientific) and converted to cDNA with using a reverse transcriptase kit sold under the trademark SUPERSCRIPT® III First-Strand Synthesis System (Invitrogen). Contaminating VL cDNA from the P3X63Ag8.653 cells were labeled using 5'-biotinylated P3 CDR-L3 primers (5'-CAGCACATTAGGGAGCTTA-CACG-3'; SEQ ID NO:11) (IDT) and then removed using Streptavidin-linked beads. The enriched cDNA was amplified using primers K6b and revCk for VL, and primers H2 and IgG2a for VH. Both VL and VH amplicons were sequenced using Sanger sequencing and annotated in NCBI igBLAST with an IMGT number (Ye, et al. (2013) *Nucleic Acids Res* 41:W34-40). The above-referenced K6b, revCk, H2 and IgG2a primers were as previously described (Essono, et al. (2003) *J. Immunol. Meth.* 2:251-66). IMGT numbers for VL and VH were entered into the SAbPred modeling software to generate a Protein Data Bank (PDB) file. The PDB for P4D2 VL/VH was entered, along with the Galectin-9 crystal structure (PDB ID: 3WV6) into the SAbPred epitope modeling software to identify binding sites (Dunbar, et al. (2016) *Nucleic Acids Res* 44:W474-478).

Cell Lines. The murine malignant mesothelioma cell line, AB12, derived from asbestos-induced tumors in a BALB/c mouse is known in the art (Davis, et al. (1992) *Int. J. Cancer* 52:881-886). The human malignant mesothelioma cell line REN is also known in the art (Smythe, et al. (1994) *Ann. Thorac. Surg.* 57(6):1395-401). Human malignant mesothelioma cell lines Mill and ROB have been previously characterized (Pass, et al. (1995) *Ann. Thorac. Surg.* 59:835-844). The human mesothelioma cell line Hmeso was obtained from the American Type Culture Collection (Manassas, VA). Murine malignant mesothelioma cell lines CRR5, EOH6 and EOH9 were isolated from peritoneal ascites developed in asbestos- or erionite-injected mice in carcinogenesis experiments previously described (Bertino, et al. (2013) *Int. J. Cancer* 133:612-23). All human and murine cells were cultured in Ham's F12 culture medium (Corning) containing 10% FBS and antibiotics.

Flow Cytometry Analysis of P4D2 Binding to Malignant Mesothelioma Cells. Mouse and human malignant mesothelioma cells were cultured for 24 hours in Ham's F12 supplemented with 2% FBS. Cells were then washed and stained for 1 hour at 4° C. with either P4D2 monoclonal antibody or IgG2 isotype control clone MG2a-53 conjugated with fluorescein isothiocyanate (FITC) using a conjugation kit sold under the trademark LIGHTING-LINK® (Innova Bioscience; Cambridge, UK). Cells were then analyzed using LSRFortessa™ (BD Biosciences) flow cytometer and analyzed with FlowJo software.

Evaluation of Malignant Mesothelioma Cell Viability and Apoptosis. Mouse (CRR5 and EOH6) and human (Mill and ROB) malignant mesothelioma cell viability was assessed by an MTT assay. Briefly, 2000 malignant mesothelioma cells were plated in each well of a 96-well plate in Ham's F12 culture medium containing 10% FBS. After 24 hours, cells were treated in reduced FBS (2%) with 20 µg/ml of either P4D2 or P1D9 monoclonal antibody. In experiments with mouse cells, mG9NC was also used at µg/ml. In experiments with human cells, hG9NC was used at 2 µg/ml. Controls were left untreated in Ham's F12 2% FBS. In these assays, the lowest monoclonal antibody and recombinant protein concentrations that induced significant effects in preliminary experiments were used. Viability was evaluated by MTT assay in triplicate for each condition every 24 hours. Fold-increases in viability were calculated by dividing the value of each day with the viability measured at day 1, before monoclonal antibody treatment. Apoptosis vs. necrosis was evaluated in malignant mesothelioma cells using flow cytometric analysis of $1 \times 10^6$ malignant mesothelioma cells cultured as above described. These cells were collected after 48 hours using a non-enzymatic cell dissociation solution sold under the trademark CELLSTRIPPER® (Corning) and stained with V500-conjugated Annexin V (BD Biosciences) and propidium iodide (PI) cell viability dye (Biolegend). Percentages of early (PI/Annexin V+) and late (PI+/Annexin V+) apoptotic cells were assessed using LSRFortessa™ (BD Biosciences) flow cytometer and FlowJo software.

Monocyte-to-Macrophage Differentiation. The effects of P4D2 monoclonal antibody, P1D9 monoclonal antibody and recombinant Galectin-9 on monocyte-to-macrophage differentiation were evaluated on both mouse bone marrow-derived monocytes (mBMDM) and human blood-derived monocytes (hBDM). For mBMDM, marrow was flushed from femurs and tibiae with Hank's Balanced Salt Solution (HESS), using a syringe with a 25-gauge needle, and cell suspensions were then passed through a 40 μm pore cell strainer to remove tissue debris. mBMDMs were plated in DMEM (ThermoFisher), containing 10% FBS and antibiotics. Differentiation of mBMDMs was induced with either 20 ng/ml or 40 ng/ml recombinant macrophage colony-stimulating factor (M-CSF) (BioLegend). In these experiments, cells were also incubated for 7 days with either 20 μg/ml P4D2 monoclonal antibody, 20 μg/ml P1D9 monoclonal antibody, or μg/ml mG9NC. Control cells were left untreated and media replaced at day 4. In other experiments, differentiation of mBMDMs was induced using 50% of the media from CRH5 malignant mesothelioma cells treated with 20 μg/ml P4D2 monoclonal antibody for 48 hours. Media from untreated CRH5 malignant mesothelioma cells was used as control. After 7 days, differentiated mBMDMs were incubated with Fc-Block™ (BD Biosciences) for 15 minutes on ice, followed by incubation with anti-F4/80-FITC clone BM8 and anti-CD38-PE clone 90 (BioLegend) for M1 macrophage staining. A fixation/permeabilization kit was used in combination with anti-Egr2-APC clone erongr2 (ThermoFisher) to stain M2 macrophage. Live cells were distinguished from debris using Zombie Violet™ cell viability dye (BioLegend). Cells were analyzed on an LSR-Fortessa™ (BD Biosciences) and analyzed with FlowJo software. Blood for hBDM was obtained from healthy volunteers under an approved protocol. Monocytes were isolated using a polysucrose and sodium diatrizoate reagent sold under the trademark HISTOPAQUE®-1077 (Sigma-Aldrich) and cultured in X-Vivo™ 10 culture media (Bio-Whittaker) containing 5% AB serum (Sigma-Aldrich) with either anti-galectn-9 P4D2 or P1D9 monoclonal antibodies (20 μg/ml), hG9NC (2 μg/ml), or no antibody for untreated control cells. Cells were incubated with fresh media on day of culture, and fully differentiated human macrophages were analyzed by flow cytometry on day 6 of culture. Anti-CD71-PE clone CY1G4, anti-CCRSAPC/Cy7 clone J418F1 and anti-CD68-APC clone FA-11 antibodies were used to characterize mature human macrophages. Surface/intracellular staining and flow cytometer analysis were performed as above described.

Murine Therapeutic Experiments. To evaluate tumor dimensions and survival, subcutaneous (s.c.) mouse models of malignant mesothelioma were employed. In these experiments, $10^5$ CRH5 or EOH6 cells were injected in the hind flank in cohorts of 5 BALB/c mice. When tumors became palpable on day 7 (3-4 mm in maximal diameter), mice received an i.p. injection of 400 μg of either of the anti-Galectin-9 monoclonal antibodies clone P4D2 or clone P1D9. A second dose of the monoclonal antibody was given 7 days later. Tumor size was measured weekly using a digital caliper until the first death was recorded. Survival was then followed until tumors reached volumes of greater than 1000 mm³ for CRH5 tumors and greater than 200 mm³ for slow growing EOH6 cells.

Survival was also evaluated in an i.p. model of malignant mesothelioma. In these experiments, CRH5 cells ($10^5$ in 100 μl PBS) were injected i.p. in cohorts of 5 BALB/c mice. Anti-Galectin-9 P4D2 monoclonal antibody injections i.p. started 7 days later when, in preliminary experiments, tumor nodules of 0.5 mm in diameter were detectable in the peritoneal cavity. Mice received a total of 4 injections with 200 μg of anti-Galectin-9 (P4D2) monoclonal antibody at days 7, 10, 13, 16, 19 and 22. Animals were monitored weekly and euthanized as soon as they appeared moribund according to IACUC guidelines.

Isolation of Tumor-Infiltrating Immune Cells and Flow Cytometer Analysis. CRH5 cells ($10^5$) were injected s.c. in cohorts of 5 BALB/c mice. When tumors reached 50 mm in maximal diameter, mice received an i.p. injection of 400 μg of anti-Galectin-9 (P4D2) monoclonal antibody. A second dose of monoclonal antibody was given 7 days later and tumors excised after another 7 days. Tissues were washed with PBS, minced and incubated for 1 hour at 37° C. in digestion buffer composed of Ham's F12 with 10% FBS, 1 mg/ml collagenase IV, 100 μl/ml hyalurodinase and 15 mg/ml DNAse I (all from Roche Applied Sciences). After digestion, tumors were forced through a 40 μm cell strainer. A total of $10^6$ cells were stained for flow cytometer analysis and macrophages were characterized as described above. In experiments to characterize tumor-infiltrating lymphocytes, the following antibodies were instead used: anti-CD3-APC/Cy7 clone OKT3, anti-CD4-PE/Dazzle 594 clone RM4-5, anti-CD8-PE/Cy5 clone 53-6.7, anti-Ki67-FITC clone 16A8, anti-CD25-APC clone PC61, anti-FoxP3-PE clone MF-14 (all from BioLegend) and Annexin V-V500 (BD Biosciences).

Analysis of RNA Expression. RNA was extracted from tumor pellets or cells using a kit sold under the trademark RNEASY® and treated with RNase-free DNase I (all from Qiagen). Synthesis of cDNA was performed using a reverse transcriptase sold under the trademark SUPERSCRIPT® III (Invitrogen) and oligo dT primers. For real-time PCR, 1 μl of cDNA was used in 10 μl reactions using Platinum™ SYBR™ Green qPCR SuperMix (Invitrogen) carried out in a LightCycler 480 II thermal cycler (Roche). Oligonucleotides used for PCR included primers specific for the housekeeping gene β-actin, murine iNOS and arginase 1. For the analysis of hBDM maturation, specific primers were used for the housekeeping gene Ubiquitin C (UBC), human CD68 and MARCO. Cycling conditions were used as suggested in the SYBR™ Green kit instructions and results analyzed using Relative Quantification Software (Roche). For cytokine measurements, tumors were collected, weighed and digested as above described. Supernatants were collected by centrifugation and cytokine levels were quantified with the cytometric bead assay mouse inflammation kit using the FACScalibur™ flow cytometer (BD Biosciences).

Immunofluorescence. Frozen sections of CRH5 tumors were fixed with 4% paraformaldehyde, blocked for endogenous biotin activity and then incubated overnight at 4° C. with 1:300 anti-F4/80-FITC clone BM8 (BioLegend). Slides were counterstained and mounted using DAPI mounting medium (VectarLab). Expression of F480 was evaluated with an Axioskop 2 plus fluorescent microscope (Zeiss). Percentage of F480⁺ cells was evaluated on 10 fields with at least 100 cells in the same slide using ImageJ software.

Transcriptome Microarray Analysis. Total RNA from BALE/c malignant mesothelioma tumors and normal tissues was extracted and evaluated using the Clariom™ S Mouse Array (Affymetrix). Expression values were normalized and summarized into transcript clusters for analysis using Robust Multi-array Average (RMA) approach in Array Studio (version 10; OmicSoft, Cary, NC). One-way ANOVA was used to look for differential expression between normal and tumor samples, and P values were adjusted for multiple comparisons using the Benjamini-Hochberg (BH) false discovery rate (FDR) method. Only candidates with FDR-adjusted p-value <0.05 were considered. The list of differentially expressed genes related with either Galectin-9 or macrophage activity, was assessed by using a web-based software application marketed under the trademark Ingenuity® Pathway Analysis (IPA)(Qiagen).

Statistics. All statistical tests were performed using GraphPad Prism (GraphPad 5.0). Means of two groups were compared using one-tailed paired Student's t-test. When more than two groups were compared, two-way ANOVA followed by the Bonferroni multiple comparison test was conducted. For survival studies, differences were evaluated using Kaplan-Meier curves with log-rank test. Both in vitro and in vivo experiments have been repeated. Data are represented as mean±s.e.m. with statistical significance values indicated together with the n values used to calculate the statistics. All experiments have been repeated multiple times using samples from the same source as technical replicates.

Example 2: Malignant Mesothelioma Tumors Express Galectin-9

Galectin-9 has been shown to be expressed in several human tumor tissues in which it modulates tumor progression, metastasis and apoptosis, as well as serving as a predictor of patient survival. Furthermore, Galectin-9 regulates anti-tumor immunity and the activity of tumor-infiltrating macrophages and interferes with cancer growth (Daley, et al. (2017) *Nat. Med.* 23:556-67). In malignant mesothelioma, macrophages play a crucial role in both carcinogenesis and disease progression (Carbone, et al. (2012) *J. Cell Physiol.* 227:44-58). The role of Galectin-9 has not been established in human malignant mesothelioma. To investigate the expression of Galectin-9, immunohistochemistry staining of 16 malignant mesothelioma samples and 3 normal mesothelial lining samples was performed. This analysis indicated that 14 out of 16 malignant mesothelioma samples showed extensive and detectable levels of Galectin-9 staining, ranging from focally to diffusely positive, while in contrast, Galectin-expression was very low to undetectable in the normal mesothelial lining samples. Notably, Galectin-9 staining was localized to the both the nucleus and cytoplasm of tumor cells.

In malignant mesothelioma, macrophages play a crucial role in both carcinogenesis and disease progression. Since Galectin-9 regulates the activity of tumor-infiltrating macrophages and the role of Galectin-9 has not been demonstrated in malignant mesothelioma animal models, a whole transcriptome analysis was performed to compare expression of Galectin-9 related transcripts and macrophage activation marker transcripts between malignant mesothelioma mouse tumors and normal tissues. In this study, tumors from 2 different mouse malignant mesothelioma cell lines, CRH5 and EOH6 were used. As normal tissues, kidney tissues that were poorly infiltrated with macrophages along with lungs that had a high content of alveolar macrophages were used. IPA software was used to identify genes that had been implicated in Galectin-9 signaling pathways. This analysis identified 19 transcripts (Ccl2, Ccl7, Cxcl10, Ccl8, Cxcl9, Pf4, Cklf, Havcr2, Ccl24, Cxcl1, Il13, Cxcl5, Cxcl11, Ccl11, Cxcl14, Ifngr2, Ccl9, Clec7a, and Cxcl16) upregulated in both malignant mesothelioma tumors when compared with the kidney. Among these, 18 transcripts were upregulated in both tumors when compared with lung. Markers were analyzed for macrophage activity. These included Csf1, which produces M-CSF that promotes monocyte-macrophage differentiation; Nos2, which encodes iNOS and serves as a marker for M1 macrophages; Arg1, which encodes arginase 1 and serves as a marker for M2 macrophages; Tnf and Il4, which encode TNFα and IL-4, respectively, that are the major cytokines that regulate the activity of M2 tumor-promoting macrophages. All of these transcripts were upregulated when compared with the kidney, and Tnf, Arg1, and Csf1 were increased in both tumors in comparison with both normal tissues.

Example 3: Anti-Galectin-9 Monoclonal Antibodies

Since malignant mesothelioma tumors overexpress molecules involved with Galectin-9 pathways, a series of anti-Galectin 9 monoclonal antibodies were generated and their capacity to interfere with these mechanisms and hinder malignant mesothelioma progression was investigated. Mice were injected with a stable form of human Galectin-9 (hG9NC) lacking the linker peptide that binds the two CRD, which is highly susceptible to proteolysis. From these mice, 8 hybridomas were generated and their secreted monoclonal antibodies were evaluated for binding to human and mouse Galectin-9. In this assay, all 8 monoclonal antibodies bound to human Galectin-9, but only P4D2 and PID9 also interacted with murine Galectin-9. The binding of the two anti-Galectin-9 monoclonal antibody clones, P4D2 and PID9 to the two versions of recombinant human Galectin-9, with (hGalectin-9M) or without (hG9NC) the linker peptide was evaluated. Both monoclonal antibodies showed binding to both versions of Galectin-9. When the two monoclonal antibodies were tested for their binding to different Galectins, limited cross-reactivity of the P4D2 clone with human Galectin-4, -7 and -8 was observed, although at a lower level compared with Galectin-9. The PID9 monoclonal antibody did not bind any other Galectin except Galectin-9. Isotyping analysis of these antibodies revealed that the anti-Galectin-9 P4D2 clone was an IgG2a antibody and the PID9 an IgG2b antibody.

Example 4: Differential Binding of Anti-Galectin-9 Monoclonal Antibodies

Galectin-9 contains two carbohydrate recognition domains in the N- and C-terminal regions. N-CRD and C-CRD of Galectin-9 have been shown to have different activities with the former involved in the regulation of innate immune cells and the latter more effective in inducing T cell apoptosis (Li, et al. (2011) *Mol. Immunol.* 48:670-77). To identify the CRD recognized by each of the anti-Galectin-9 monoclonal antibodies P4D2 and PID9, two fusion proteins, hG9G8 and hG8G9, each which has one of the CRDs from Galectin-9 substituted with the CRD from Galectin-8 were generated. The fusion protein hG9G8 includes the N-terminal CRD from human Galectin-9 with the Galectin-8 C-terminal CRD. Conversely, hG8G9 includes the N-terminal CRD from human Galectin-8 and the C-terminal CRD from Galectin-9. ELISA plates were coated with these two fusion proteins, and binding of the two anti-Galectin-9 monoclonal antibodies (P4D2 or P1D9) was evaluated. In these experiments, P4D2 showed strong binding with hG8G9, containing the C-terminal region of Galectin-9. Binding of the P4D2 clone to hG9G8 was significantly reduced compared with binding to hG8G9. In contrast, the P1D9 monoclonal antibody showed stronger binding with hG9G8 than with hG8G9. To further characterize the interaction between the anti-Galectin-9 monoclonal antibodies and Galectin-9, the Fv of the P4D2 clone was sequenced and the information was used to design a digital model of this monoclonal antibody. Simulation modeling between the digital prototype of P4D2 clone and the crystal-structure of Galectin-9 using SAbPred was performed. This analysis confirmed binding of anti-Galectin-9 P4D2 monoclonal antibody to the C-terminus of Galectin-9. The predicted Galectin-9 amino acids involved in the interaction with the Fv of P4D2 monoclonal antibody included amino acid residues 204-205, 228-232, 250-254, 256-257, 259, 281-283 and 298-306 of Galectin-9.

Example 5: Anti-Galectin-9 P4D2 Monoclonal Antibody

Agonizes Malignant Mesothelioma Cell Apoptosis

Recombinant Galectin-9 has been demonstrated to induce apoptosis in different types of tumor cells (Kuroda, et al. (2010) *Mol. Cancer Res.* 8:994-1001; Kobayashi, et al. (2010) *Leukemia* 24:843-850; Wiersma, et al. (2012) *J. Invest. Dermatol.* 132:2302-2305; Fujita, et al. (2015) *Int. J. Oncol.* 46:2419-2430; Kobayashi, et al. (2015) *Oncol. Rep.* 34:1761-70; Tadokoro, et al. (2016) *Int. J. Oncol* 48:1165-1174; Tadokoro, et al. (2016) *Oncol. Rep.* 35:851-860), but its effects on malignant mesothelioma cell death are unknown. In initial experiments, it was observed that both human and mouse malignant mesothelioma cells express Galectin-9 on their surface. Therefore, the effects of the P4D2 and P1D9 anti-Galectin-9 monoclonal antibodies on malignant mesothelioma cells was investigated. In these experiments, two human malignant mesothelioma cell lines (Mill and ROB) and two mouse malignant mesothelioma cell lines (CRH5 and EOH6) were assayed. In Mill cells, a reduction of viability during P4D2 monoclonal antibody treatment compared with untreated controls at days 2, 3, 4 and 5 was observed. In these cells, stable human recombinant Galectin-9 (hG9NC) also reduced cell viability starting from day 2 until the end of the assay at day 5 (FIG. 1). In ROB cells, both P4D2 monoclonal antibody and hG9NC reduced viability significantly starting from day 2 until the end of the assay at day 5. In CRH5 cells, the P4D2 monoclonal antibody significantly reduced cell viability for the entire duration of the experiment from day 1 to day 5. Stable mouse Galectin-9 (mG9NC) also decreased cell viability but only at day 5. In EOH6 cells, both P4D2 monoclonal antibody and mG9NC reduced viability at day 3 through the end of the assay.

Figure 2:
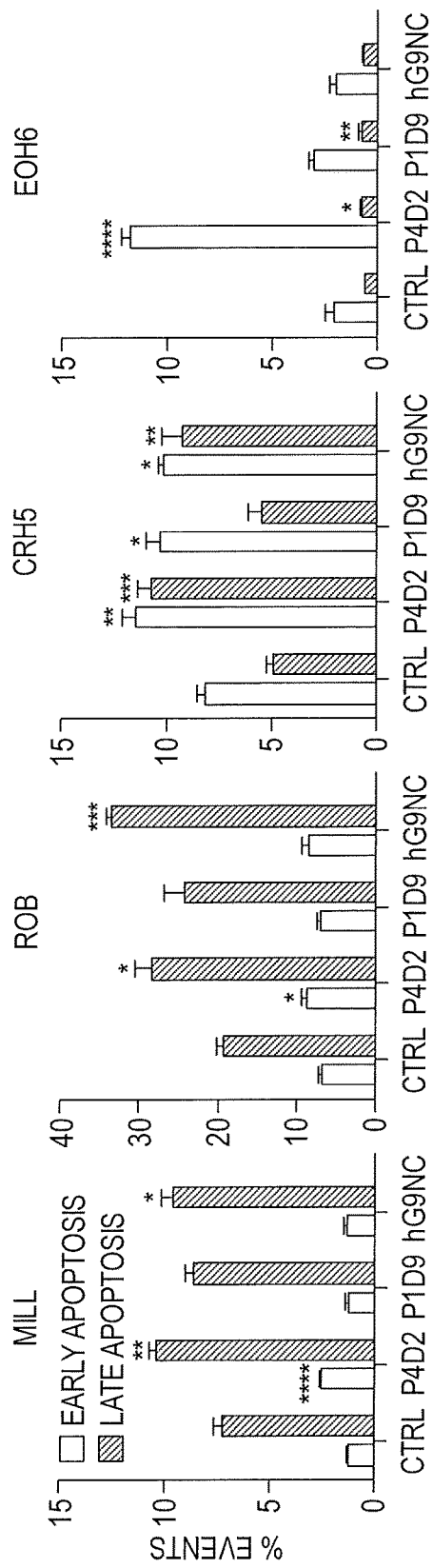
FIG. 2 provides data demonstrating that anti-Galectin-9 P4D2 monoclonal antibody exerts agonist effects in inducing apoptosis in malignant mesothelioma cells. Apoptosis versus necrosis was assessed by flow cytometry for human (ROB and MilI) and mouse (CRH5 and EOH6) malignant mesothelioma cells treated with anti-Galectin-9 monoclonal antibody P4D2 or P1D9, or hG9NC. Percentages of $PI^-$/Annexin $V^+$ (early apoptotic) cells and $PI^+$/Annexin $V^+$ (late apoptotic) cells are shown. Statistically significant differences between treatment and no treatment (Ctrl) were assessed with two-way ANOVA followed by the Bonferroni test and indicated P≤0.01 (*), n=3.

The degree of apoptosis by the anti-Galectin-9 monoclonal antibody treatment of malignant mesothelioma cells using a combination of propidium iodide (PI) and Annexin V co-staining was also investigated. In Mill cells, hG9NC, P1D9 and P4D2 monoclonal antibodies induced higher percentages of PI$^+$/Annexin V$^+$ cells representing late apoptotic cells, compared with untreated malignant mesothelioma cells (FIG. 2). Also, an increase in early apoptotic cells (PI$^-$/Annexin V$^+$) was detected with P4D2 monoclonal antibody treatment. In ROB cells, an increase in both early and late apoptotic cells for P4D2 monoclonal antibody was observed, while hG9NC treatment induced only an increase in late apoptotic cells. In CRH5 cells, both P4D2 monoclonal antibody and mG9NC induced higher percentages of late apoptotic cells compared with untreated controls. In these cells, a significant increase in the numbers of early apoptotic cells was assessed also for both treatments (anti-Galectin-9 P4D2 monoclonal antibody and recombinant mG9NC) when compared with controls. In EOH6 cells, P4D2 monoclonal antibody was the only treatment that induced higher percentages of both early and late apoptotic cells when compared with untreated controls. No differences in necrotic cells populations (PI$^+$/Annexin V$^-$) were found among the different conditions for all mesothelioma cells.

Example 6: P4D2 Monoclonal Antibody Modulates Human Monocyte Differentiation with Reduced Formation of Pro-Tumor Macrophages It has been reported that blockage of Galectin-9 shifts tumor-infiltrating macrophages toward an anti-tumor phenotype and protects against tumor progression (Daley, et al. (2017) *Nat. Med.* 23:556-567). Studies were conducted to determine if the anti-Galectin-9 monoclonal antibodies can alter monocyte differentiation or reduce formation of pro-tumor myeloid cells. Human primary monocytes were differentiated with human AB serum in the presence of either P4D2 or P1D9 anti-Galectin-9 monoclonal antibodies and compared to the effects of a human stable recombinant Galectin-9 (hG9NC) as control. After one week of culture in these conditions, cells were analyzed by flow cytometry for cell surface levels of CD68 and CCR5. CD68 is a marker highly expressed by cells of the monocyte lineage, including circulating and tissue macrophages (Holness, et al. (1993) *Blood* 81:1607-13), while CCR5 increases during monocyte-macrophage differentiation and is responsible for the recruitment of TAMs in the tumor microenvironment (Aldinucci & Colombatti (2014) *Mediators Inflamm*. Article ID 292376). The data showed a significant reduction in CD68$^+$ CCR5$^+$ mature macrophages after treatment with either P4D2 monoclonal antibody (~7.5%) or hG9NC (~5%), compared with control cells (~12.5%) differentiated in AB serum without any treatment. Interestingly, the number of live cells significantly increased with the P4D2 monoclonal antibody treatment, suggesting that P4D2 monoclonal antibody blocks monocyte differentiation rather than killing mature macrophages. In contrast, P1D9 monoclonal antibody displayed the same percentage of CD68$^+$ CCR5$^+$ cells as controls (~12%). Monocyte-macrophage differentiation was induced using supernatants from human ROB malignant mesothelioma cells treated or untreated with P4D2 monoclonal antibody. In these assays, the number of CD68$^+$ CCR5$^+$ cells was sharply reduced when the supernatant from P4D2-treated ROB malignant mesothelioma cells was used (~19%), compared with controls cultured with supernatant of untreated ROB malignant mesothelioma cells (~45%). Real-time PCR was used to assess mRNA levels for CD68 and the macrophage receptor with collagenous structure (MARCO) in cells differentiated with supernatants from either untreated human ROB malignant mesothelioma cells or treated with P4D2 monoclonal antibody. MARCO is a marker expressed by immune-suppressive TAMs, linked to poor prognosis in cancer patients (Georgoudaki, et al. (2016) *Cell Rep.* 15:2000-2011). Macrophages differentiated with the supernatant from P4D2-treated ROB malignant mesothelioma cells showed decreased MARCO mRNA compared with cells differentiated with the supernatant from untreated ROB malignant mesothelioma cells. Levels of CD68 did not change between the two conditions.

Example 7: Anti-Galectin-9 P4D2 Monoclonal Antibody Shifts Mouse Monocyte Differentiation Toward an M1 Phenotype As demonstrated here, the P4D2 monoclonal antibody hinders human monocyte maturation to tumor-promoting macrophages. Thus, it was determined whether the same effect was observed in mouse bone marrow-derived macrophages (BMDMs). In these assays, four different conditions were used to induce BMDM differentiation to macrophages: (1) M-CSF, a conventional approach as well as a cytokine found up-regulated in mouse malignant mesothelioma tumors; (2) M-CSF plus P4D2 monoclonal antibody; (3) supernatants from mouse malignant mesothelioma CRH5 cells; and (4) supernatants from CRH5 cells treated with the P4D2 monoclonal antibody. Flow cytometry was used to measure F480$^+$ cells as a marker that identifies mouse macrophages. Results showed a significant increase in F480+ macrophages in cultures using the supernatant from P4D2 monoclonal antibody-treated malignant mesothelioma cells (~11%) when compared to cells cultured with the supernatant from untreated malignant mesothelioma cells (~7%). No differences were observed between cells differentiated with M-CSF with or without P4D2 monoclonal antibody. F480+ cells were further characterized using markers for M1 anti-tumor (CD38$^{hi}$) and M2 pro-tumor (Egr2$^+$) macrophages. With both M-CSF or CRH5 media used as maturation stimuli, a significant increase in M1 F480+ CD38$^{hi}$ macrophages was observed when P4D2 monoclonal antibody was employed. Regarding M2 macrophages, a complete lack of differentiation into these cells was observed in the presence of P4D2 monoclonal antibody, either when BMDMs were differentiated with M-CSF or CRH5 media. When M1 and M2 ratios were calculated, an increase toward the M1 phenotype for cells treated with P4D2 monoclonal antibody and M-CSF (ratio of ~1:900) was observed compared with cells treated with M-CSF (1:1), and for BMDMs cultured with the supernatant from P4D2 monoclonal antibody-treated malignant mesothelioma cells (ratio of ~1:500) compared with those cultured with supernatant from untreated CRH5 malignant mesothelioma cells (1:1). For all these conditions, no statistically significant differences in the number of live cells were detected. Experiments were also performed to evaluate the effects of P4D2 monoclonal antibody during BMDM differentiation induced with high dosages of M-CSF. As observed for lower doses of M-CSF, P4D2 monoclonal antibody strongly reduced the percentages F480+ cells, but the number of live cells was also dramatically reduced. Surprisingly, stable recombinant mouse Galectin-9 (mG9NC) also decreased numbers of F480+ cells, but viability was not altered, even at high concentrations of M-CSF.

Figures 3, 4, 5:
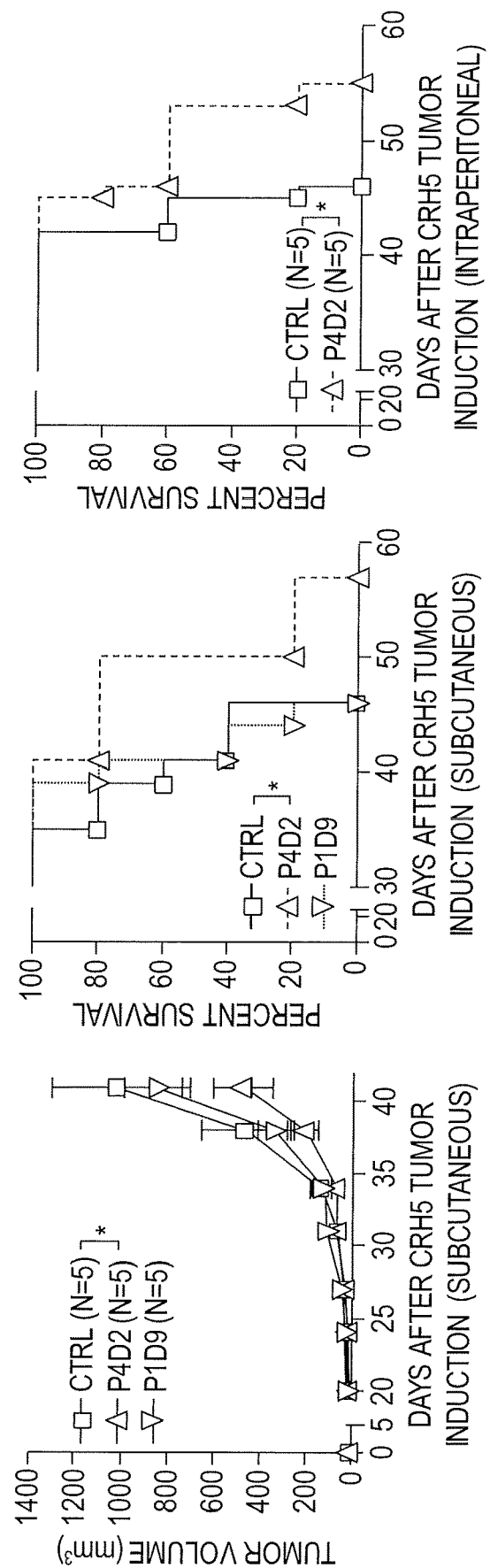
FIG. 3 provides data demonstrating that treatment with anti-Galectin-9 P4D2 monoclonal antibody hinders tumor growth in an animal model with subcutaneous malignant mesothelioma injection. BALB/c mice with subcutaneous CRH5 malignant mesothelioma tumors were treated with anti-Galectin-9 monoclonal antibodies P4D2 or PID9. Control mice were left untreated. Tumor dimensions are shown for the different treatments. Differences between control (Ctrl) and anti-Galectin-9 P4D2 monoclonal antibody groups were compared with ANOVA followed by the Bonferroni multiple comparison test (n=5/group) and indicated with *P≤0.01.
FIG. 4 provides data demonstrating that treatment with anti-Galectin-9 P4D2 monoclonal antibody improves survival in an animal model with subcutaneous malignant mesothelioma injection. Mice treated with anti-Galectin-9 P4D2 monoclonal antibody (n=5/group) showed increased survival compared to controls *P≤0.01.
FIG. 5 provides data demonstrating that treatment with anti-Galectin-9 P4D2 monoclonal antibody improves survival in an animal model with intraperitoneal malignant mesothelioma injection. Differences in anti-Galectin-9 P4D2 monoclonal antibody treated vs. controls were evaluated using Kaplan-Meier curves with log-rank test and indicated with *P≤0.01 and n=5.

Example 8: In Vivo Anti-Galectin-9 P4D2 Monoclonal Antibody Treatment Hinders Tumor Growth and Improves Survival The above-referenced findings show that P4D2 monoclonal antibody can induce mouse malignant mesothelioma cell apoptosis and can reduce M2 pro-tumor macrophage formation from mouse BMDMs. Thus, experiments were carried out to verify the potential anti-tumor effect of P4D2 monoclonal antibody in animal models of malignant mesothelioma. BALB/c mice were inoculated s.c. with either CRH5 or EOH6 malignant mesothelioma cells. When tumors reached 3-4 mm in diameter, mice were i.p. injected with 400 μg of P4D2 monoclonal antibody followed by another injection of the same dose 7 days later. Control mice were left untreated or injected with P1D9 monoclonal antibody. Treatment with P4D2 monoclonal antibody resulted in reduced tumor growth compared to controls for both malignant mesothelioma cells (FIG. 3). Survival analyses revealed that P4D2 injected mice, carrying CRH5 tumors, also exhibited prolonged median survival compared with untreated controls and P1D9-treated mice (FIG. 4).

Since malignant mesothelioma develops from mesothelial cells lining internal body cavities, a clinically relevant peritoneal malignant mesothelioma model was developed for testing the therapeutic efficacy of P4D2 monoclonal antibodies. In these experiments, CRH5 malignant mesothelioma cells were injected into the peritoneum of two groups of BALE/c mice. Seven days later, when tumors started growing and spreading within the peritoneal cavity, mice were treated with P4D2 monoclonal antibody or left untreated. Survival analyses showed a significant increase in median survival of P4D2 monoclonal antibody-treated mice compared to control animals (FIG. 5). In all the animal models treated with P4D2 monoclonal antibody, no adverse events such as acute effects, distress, or weight loss were observed, and gross tissue examination failed to indicate any toxicity in the organs (kidney, brain, spleen, liver and lungs).

Example 9: Treatment with Anti-Galectin-9 P4D2 Monoclonal Antibody Alters Intra-Tumor Macrophages M1/M2 Ratio with Increased Production of INOS and Reduced Cytokines Tumors were characterized from mice treated with P4D2 monoclonal antibody and untreated controls. Immunofluorescence staining using FITC-conjugated F480 antibodies revealed a reduced number of TAMs in tumors from mice treated with P4D2 monoclonal antibodies (~2% F480+ cells) compared with untreated controls (~8% F480+ cells). Flow cytometry results confirmed these data showing lower percentages of F480+ macrophages in tumors from P4D2-treated mice compared with controls. Analysis of TAMs for markers for M1 (CD38$^{hi}$) and M2 (Erg2) macrophages showed that mice injected with P4D2 monoclonal antibody had reduced percentages of F480+ CD38$^{hi}$ M1 cells (~6% vs. ~14%) and F480+ Egr2+ M2 macrophages (~3.5% vs. ~11.5%) compared with untreated controls. Analysis of iNOS and arginase 1 mRNA produced by M1 and M2 macrophages, respectively, showed higher production of iNOS mRNA for P4D2-treated mice compared to controls, but no differences in arginase 1 mRNA levels.

To evaluate if P4D2 monoclonal antibody skews macrophage differentiation toward the M1 phenotype in vivo, ratios between M1 and M2 macrophages were calculated using data from flow cytometry and real-time PCR. In both cases, ratios were significantly higher for P4D2 monoclonal antibody-treated mice indicating a prevalence of M1 iNOS-secreting TAMs in these mice.

T cell frequency, proliferation, and granzyme B secretion were also analyzed in tumors from mice treated with P4D2 monoclonal antibody or untreated. Importantly, no differences were recorded for any of these parameters. Also, markers for T regulatory cells (CD25 and FoxP3) were analyzed in tumors from P4D2 monoclonal antibody treated mice, and no differences were detected compared to control, untreated mice.

What is claimed is:

1. An isolated antibody, or an antigen binding fragment of the antibody, which binds human Galectin-9, wherein the antibody comprises:
   (a) a heavy chain variable region comprising,
      (i) a CDR1 of SEQ ID NO:1;
      (ii) a CDR2 of SEQ ID NO:2; and
      (iii) a CDR3 of SEQ ID NO:3; and
   (b) a light chain variable region comprising,
      (i) a CDR1 of SEQ ID NO:4,
      (ii) a CDR2 of SEQ ID NO:5, and
      (iii) a CDR3 of SEQ ID NO:6.

2. The isolated antibody of claim 1, wherein the antibody comprises a heavy chain variable region of SEQ ID NO:7 and a light chain variable region of SEQ ID NO:8.

3. A pharmaceutical composition comprising the antibody or antigen binding fragment of claim 1 in admixture with a pharmaceutically acceptable carrier.

4. An isolated nucleic acid encoding the antibody or antigen binding fragment of claim 1.

5. A host cell comprising the isolated nucleic acid of claim 4.

6. A method of inhibiting Galectin-9-mediated cell signaling in a subject comprising administering to a subject in need thereof an effective amount of a pharmaceutical composition of claim 3 thereby inhibiting Galectin-9-mediated cell signaling in the subject.

7. The method of claim 6, wherein the subject is a human patient having, suspected of having, or at risk for having, an autoimmune disease, a cancer, or a microbial disease.

8. The method of claim 7, wherein the cancer is malignant mesothelioma.

9. The method of claim 6, further comprising administering to the subject an inhibitor of a checkpoint molecule, an activator of a co-stimulatory receptor, or a combination thereof.

10. The method of claim 9, wherein the checkpoint molecule is selected from the group of PD-1, PD-L1, PD-L2, CTLA-4, LAG3, TIM-3, TIGIT and A2aR.

11. The method of claim 9, wherein the co-stimulatory receptor is selected from the group of OX40, GITR, CD137, CD40, CD27, and ICOS.

12. A method for treating cancer in a subject comprising administering to a subject in need thereof an effective amount of a pharmaceutical composition of claim 3 thereby treating the subject's cancer.

13. The method of claim 12, wherein the cancer is malignant mesothelioma.

14. The method of claim 12, further comprising administering to the subject an inhibitor of a checkpoint molecule, an activator of a co-stimulatory receptor or a combination thereof.

15. The method of claim 14, wherein the checkpoint molecule is selected from the group of PD-1, PD-L1, PD-L2, CTLA-4, LAG3, TIM-3, TIGIT and A2aR.

16. The method of claim 14, wherein the co-stimulatory receptor is selected from the group of OX40, GITR, CD137, CD40, CD27, and ICOS.

* * * * *